US011267785B2

(12) United States Patent
Lanthier et al.

(10) Patent No.: US 11,267,785 B2
(45) Date of Patent: Mar. 8, 2022

(54) PROCESS FOR PREPARING [(3-HYDROXYPYRIDINE-2-CARBONYL) AMINO]ALKANOIC ACIDS, ESTERS AND AMIDES

(71) Applicant: Akebia Therapeutics, Inc., Cambridge, MA (US)

(72) Inventors: Christopher M. Lanthier, Burlington (CA); Boris Gorin, Oakville (CA); Jan Oudenes, Aurora (CA); Craig Edward Dixon, Brooklin (CA); Alan Quigbo Lu, Mississauga (CA); James Densmore Copp, Bargersville, IN (US); John Michael Janusz, Oregonia, OH (US)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/921,273

(22) Filed: Jul. 6, 2020

(65) Prior Publication Data
US 2021/0122715 A1    Apr. 29, 2021

Related U.S. Application Data

(60) Continuation of application No. 16/352,705, filed on Mar. 13, 2019, now Pat. No. 10,738,010, which is a continuation of application No. 15/692,255, filed on Aug. 31, 2017, now Pat. No. 10,246,416, which is a continuation of application No. 14/833,222, filed on Aug. 24, 2015, now Pat. No. 9,776,969, which is a division of application No. 13/488,554, filed on Jun. 5, 2012, now Pat. No. 9,145,366.

(60) Provisional application No. 61/493,536, filed on Jun. 6, 2011.

(51) Int. Cl.
*C07D 213/803* (2006.01)
*C07D 213/81* (2006.01)
*C07D 213/79* (2006.01)

(52) U.S. Cl.
CPC ......... *C07D 213/81* (2013.01); *C07D 213/79* (2013.01); *C07D 213/803* (2013.01)

(58) Field of Classification Search
CPC ................................................. C07D 213/803
See application file for complete search history.

(56) References Cited

U.S. PATENT DOCUMENTS

| 3,655,679 A | 4/1972 | Tsung-Ying et al. |
| 3,703,582 A | 11/1972 | Shen et al. |
| 3,894,920 A | 7/1975 | Kondo et al. |
| 4,016,287 A | 4/1977 | Eberhardt et al. |
| 5,397,799 A | 3/1995 | Kress et al. |
| 5,405,613 A | 4/1995 | Rowland et al. |
| 5,607,954 A | 3/1997 | Weidmann et al. |
| 5,610,172 A | 3/1997 | Weidmann et al. |
| 5,620,995 A | 4/1997 | Weidemann et al. |
| 5,620,996 A | 4/1997 | Weidmann et al. |
| 5,658,933 A | 8/1997 | Weidemann et al. |
| 5,719,164 A | 2/1998 | Weidmann et al. |
| 5,726,305 A | 3/1998 | Weidmann et al. |
| 6,020,350 A | 2/2000 | Wiedmann et al. |
| 6,093,730 A | 7/2000 | Weidmann et al. |
| 6,159,379 A | 12/2000 | Means et al. |
| 6,420,427 B1 | 7/2002 | Takahashi et al. |
| 6,566,088 B1 | 5/2003 | McKnight et al. |
| 6,589,758 B1 | 7/2003 | Zhu |
| 7,183,287 B2 | 2/2007 | Durley |
| 7,323,475 B2 | 1/2008 | Arend et al. |
| 7,588,924 B2 | 9/2009 | Evdokimov et al. |
| 7,811,595 B2 | 10/2010 | Kawamoto et al. |
| 8,050,873 B2 | 11/2011 | Evdokimov et al. |
| 8,124,582 B2 | 2/2012 | Guenzler-Pukall et al. |
| 8,129,376 B2 | 3/2012 | Sundaresan et al. |
| 8,273,773 B2 | 9/2012 | Brameld et al. |
| 8,323,671 B2 | 12/2012 | Wu et al. |
| 8,343,952 B2 | 1/2013 | Kawamoto et al. |
| 8,512,972 B2 | 8/2013 | Evdokimov et al. |
| 8,530,404 B2 | 9/2013 | Seeley et al. |
| 8,598,210 B2 | 12/2013 | Kawamoto et al. |
| 8,722,895 B2 | 5/2014 | Kawamoto et al. |
| 8,865,748 B2 | 10/2014 | Shalwitz et al. |

(Continued)

FOREIGN PATENT DOCUMENTS

| CA | 2098158 | 6/1993 |
| CA | 2253282 | 11/1997 |

(Continued)

OTHER PUBLICATIONS

U.S. Appl. No. 17/053,614, filed Nov. 6, 2020, Gorin et al.

(Continued)

*Primary Examiner* — Patricia L Morris

(74) *Attorney, Agent, or Firm* — Proskauer Rose LLP; Fangli Chen

(57) ABSTRACT

Disclosed are processes for preparing [(3-hydroxypyridine-2-carbonyl)amino]-alkanoic acids, derivatives, inter alia, 5-aryl substituted and 5-heteroaryl substituted [(3-hydroxypyridine-2-carbonyl]amino}acetic acids. Further disclosed are methods for making prodrugs of [(3-hydroxypyridine-2-carbonyl)-amino]acetic acids, for example, [(3-hydroxypyridine-2-carbonyl]amino}acetic acid esters and {[3-hydroxypyridine-2-carbonyl]amino}acetic acid amides. The disclosed compounds are useful as prolyl hydroxylase inhibitors or for treating conditions wherein prolyl hydroxylase inhibition is desired.

5 Claims, 3 Drawing Sheets

(56) References Cited

U.S. PATENT DOCUMENTS

| | | |
|---|---|---|
| 8,940,773 B2 | 1/2015 | Kawamoto et al. |
| 9,145,366 B2 | 9/2015 | Lanthier et al. |
| 9,598,370 B2 | 3/2017 | Kawamoto et al. |
| 9,701,636 B2 | 7/2017 | Copp et al. |
| 9,776,969 B2 | 10/2017 | Lanthier et al. |
| 9,987,262 B2 | 6/2018 | Copp et al. |
| 10,149,842 B2 | 12/2018 | Copp et al. |
| 10,246,416 B2 | 4/2019 | Lanthier et al. |
| RE47,437 E | 6/2019 | Kawamoto et al. |
| 10,596,158 B2 | 3/2020 | Copp et al. |
| 10,729,681 B2 | 8/2020 | Kawamoto et al. |
| 10,738,010 B2 | 8/2020 | Lanthier et al. |
| 2002/0192737 A1 | 12/2002 | Kaelin, Jr. et al. |
| 2003/0153503 A1 | 8/2003 | Klaus et al. |
| 2003/0176317 A1 | 9/2003 | Guenzler-Pukall et al. |
| 2004/0235082 A1 | 11/2004 | Foumey et al. |
| 2004/0254215 A1 | 12/2004 | Arend et al. |
| 2006/0142389 A1 | 6/2006 | Aurell et al. |
| 2006/0276477 A1 | 12/2006 | Klaus et al. |
| 2007/0105899 A1 | 5/2007 | Suzuki et al. |
| 2007/0154482 A1 | 7/2007 | Sukhatme et al. |
| 2007/0203174 A1 | 8/2007 | Klimko et al. |
| 2007/0213335 A1 | 9/2007 | Fitch et al. |
| 2007/0299086 A1 | 12/2007 | Kawamoto et al. |
| 2008/0124740 A1 | 5/2008 | Evkokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2009/0240475 A1 | 9/2009 | Evdokimov et al. |
| 2010/0021423 A1 | 1/2010 | Brameld et al. |
| 2010/0331303 A1 | 12/2010 | Kawamoto et al. |
| 2010/0331374 A1 | 12/2010 | Wu et al. |
| 2011/0077400 A1 | 3/2011 | Lobben et al. |
| 2011/0305776 A1 | 12/2011 | Ho et al. |
| 2012/0282627 A1 | 11/2012 | Evdokimov et al. |
| 2012/0309977 A1 | 12/2012 | Lanthier et al. |
| 2012/0316204 A1 | 12/2012 | Shalwitz et al. |
| 2012/0329836 A1 | 12/2012 | Marsh et al. |
| 2013/0022974 A1 | 1/2013 | Chinnaiyan et al. |
| 2013/0203816 A1 | 8/2013 | Kawamoto et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0141467 A1 | 5/2015 | Copp |
| 2015/0361043 A1 | 12/2015 | Lanthier et al. |
| 2016/0009648 A1 | 1/2016 | Kawamoto et al. |
| 2016/0143891 A1 | 5/2016 | Shalwitz et al. |
| 2016/0199434 A1 | 7/2016 | Eubank et al. |
| 2016/0214939 A1 | 7/2016 | Hanselmann et al. |
| 2016/0339005 A1 | 11/2016 | Shalwitz et al. |
| 2017/0189387 A1 | 7/2017 | Kawamoto et al. |
| 2017/0258773 A1 | 9/2017 | Copp et al. |
| 2017/0362178 A1 | 12/2017 | Lanthier et al. |
| 2018/0065933 A1 | 3/2018 | Hanselmann et al. |
| 2018/0092892 A1 | 4/2018 | Smith et al. |
| 2018/0280365 A1 | 10/2018 | Copp et al. |
| 2019/0192494 A1 | 6/2019 | Kawamoto et al. |
| 2020/0345711 A1 | 11/2020 | Copp et al. |

FOREIGN PATENT DOCUMENTS

| | | |
|---|---|---|
| EP | 0650960 | 5/1995 |
| EP | 0650961 | 5/1995 |
| EP | 2044005 | 10/2010 |
| JP | H09221476 | 8/1997 |
| JP | 2001-48786 | 2/2001 |
| JP | 2007-194072 | 11/2006 |
| JP | 2010-527378 | 11/2009 |
| WO | WO 1996/022021 | 7/1996 |
| WO | WO 1997/041103 | 11/1997 |
| WO | WO 1997/044333 | 11/1997 |
| WO | WO 1999/048870 | 11/1999 |
| WO | WO 2002/074980 | 9/2002 |
| WO | WO 2002/074981 | 9/2002 |
| WO | WO 2002/083688 | 10/2002 |
| WO | WO 2003/028663 | 4/2003 |
| WO | WO 2003/032972 | 4/2003 |
| WO | WO 2003/049686 | 6/2003 |
| WO | WO 2003/053997 | 7/2003 |
| WO | WO 2003/097040 | 11/2003 |
| WO | WO 2004/019868 | 3/2004 |
| WO | WO 2004/035812 | 4/2004 |
| WO | WO 2004/048383 | 6/2004 |
| WO | WO 2004/108121 | 12/2004 |
| WO | WO 2005/007192 | 1/2005 |
| WO | WO 2005/115984 | 12/2005 |
| WO | WO 2005/118836 | 12/2005 |
| WO | WO 2006/019831 | 2/2006 |
| WO | WO 2006/030977 | 3/2006 |
| WO | WO 2006/114213 | 11/2006 |
| WO | WO 2007/047194 | 4/2007 |
| WO | WO 2007/070359 | 6/2007 |
| WO | WO 2007/082899 | 7/2007 |
| WO | WO 2007/084667 | 7/2007 |
| WO | WO 2007/088571 | 8/2007 |
| WO | WO 2007/103905 | 9/2007 |
| WO | WO 2007/136990 | 11/2007 |
| WO | WO 2007/150011 | 12/2007 |
| WO | WO 2008/002576 | 1/2008 |
| WO | WO 2008/089051 | 7/2008 |
| WO | WO 2008/089052 | 7/2008 |
| WO | WO 2009/020119 | 8/2008 |
| WO | WO 2008/130508 | 10/2008 |
| WO | WO 2008/130527 | 10/2008 |
| WO | WO 2008/137060 | 11/2008 |
| WO | WO 2008/141731 | 11/2008 |
| WO | WO 2008/144266 | 11/2008 |
| WO | WO 2009/019656 | 2/2009 |
| WO | WO 2009/035534 | 3/2009 |
| WO | WO 2009/037570 | 3/2009 |
| WO | WO 2009/039321 | 3/2009 |
| WO | WO 2009/039323 | 3/2009 |
| WO | WO 2007/038571 | 4/2009 |
| WO | WO 2009/043093 | 4/2009 |
| WO | WO 2009/049112 | 4/2009 |
| WO | WO 2009/067790 | 4/2009 |
| WO | WO 2009/070644 | 6/2009 |
| WO | WO 2009/073497 | 6/2009 |
| WO | WO 2009/073669 | 6/2009 |
| WO | WO 2009/086044 | 7/2009 |
| WO | WO 2009/086592 | 7/2009 |
| WO | WO 2009/089547 | 7/2009 |
| WO | WO 2009/111337 | 9/2009 |
| WO | WO 2010/029577 | 3/2010 |
| WO | WO 2010/113942 | 10/2010 |
| WO | WO 2011/057112 | 11/2010 |
| WO | WO 2012/170377 | 12/2012 |
| WO | WO 2012/170439 | 12/2012 |
| WO | WO 2012/170442 | 12/2012 |
| WO | WO 2013/013609 | 1/2013 |
| WO | WO 2014/168986 | 10/2014 |
| WO | WO 2014/200773 | 12/2014 |
| WO | WO 2015/023967 | 2/2015 |
| WO | WO 2015/073779 | 5/2015 |
| WO | WO 2015/112831 | 7/2015 |
| WO | WO 2016/118858 | 7/2016 |
| WO | WO 2016/153996 | 9/2016 |
| WO | WO 2016/161094 | 10/2016 |
| WO | WO 2006/138511 | 12/2016 |
| WO | WO 2019/217550 | 11/2019 |

OTHER PUBLICATIONS

"Akebia closes $41 million series C—Proceeds to support phase 2b trial and phase 3 preparations for promising anemia candidate", 2013; retrieved from the internet at <http://files.shareholder.com/downloads/AMDA-2MD7AT/0x0x733748/5e5822e6-2bcd-4969-ab79-0d298fee5066/733748.pdf> on Jan. 22, 2018.

"Hippuric acid sodium salt", Science Lab.com: Chemicals & Laboratory Equipment; retrieved from the internet at <http://web.archive.org/web/20041107121553/http://www.sciencelab.com/page/S/PVAR/10415/SLH2620> on Mar. 11, 2010.

(56) References Cited

OTHER PUBLICATIONS

"Standards of Medical Care in Diabetes—2006", Diabetes Care, 29: s4-s42 (2006).
Acker et al., "Genetic evidence for a tumor suppressor role of HIF-2α", Cancer Cell, 8:131-141 (2005).
Alesso et al., "Improving resins for solid phase synthesis: incorporation of I-[2-(2-methoxvethoxv) ethoxv]4-vinvl-benzene" Tetrahedron: 59: 7163-7169 (2003).
Altschul et al.,"Gapped BLAST and PSI-BLAST: A New Generation of Protein Database Search Programs," Nucleic Acids Res., 25(27): 3389-3402 (1997).
Anderson et al., "Antileukemic Activity of Derivatives of I,2-Dimethyl-3,4-bis(hydroxvmethyl)-5-phenylpyrrole Bis(N-methylcarbamate)", J. Med. Chem., 22(8): 977-980 (1979).
Anderson et al., "Practical process research and development: a guide for organic chemists", p. 331. (2012).
Annex et al., "Growth Factor-Induced Therapeutic Angiogenesis in the Heart: Protein Therapy," Cardiovascular Research, 65(3): 649-655 (2005).
Ardelt et al., "Estradiol Regulates Angiopoietin-1 mRNA Expression Through Estrogen Receptor-a in a Rodent Experimental Stroke Model," Stroke, 36: 337-341 (2005).
Auerbach et al., "Angiogenesis Assays: A Critical Overview," Clinical Chemistry, 49: 32-40 (2003).
Barany et al., "Solid-phase Peptide Synthesis: A Silver Anniversary Report," Int. J. Peptide Protein Res., 30( 6): 705-739 (1987).
Bartlett et al., "Caveat: A Program to Facilitate the Structure-derived Design of Biologically Active Molecules", Molecular Recognition in Chemical and Biological Problems, Special Pub., Royal Chem. Soc., 78: 182-196 (Apr. 1989).
Bohm, "The Computer Program LUDI: A New Method for the Novo Design of Enzyme Inhibitors," J. Computer-Aided Molecular Design, 6: 61-78 (1992).
Branden et al., "Introduction to Protein Structure Second Edition," Garland Publishing, Inc., New York: 374-375 (1999).
Brittain et al., "Polymorphism in Pharmaceutical Solids." Drugs and the Pharmaceutical Sciences, 2nd Edition, Edited by Brittain H.G., 192: 333-335 (2009).
Burger, "Isosterism and biososterism in drug design", Progress in Drug Research, Birkhauser Verlag (1991).
Bussolino, "Molecular Mechanisms of Blood Vessel Formation," Trends Biochem. Sci., 22(7): 251-256 (1997).
Byrn et al., "Pharmaceutical Solids: A Strategic Approach to Regularity Considerations", Pharmaceutical Research, 12(7): 945-954 (1995).
CAS Registry Nos. 1261813-98-2, 1261613-86-8, and 1261518-21-1. Chemcats, (2011).
Carey, FA., Organic Chemistry 6th Ed. McGraw Hill, chapter 1, p. 9, chapter 19, pp. 839-840 and chapter 27, pp. 1182-1183 (2006).
Catrina et al., "Hyperglycemia Regulates Hypoxia-Inducible Factor-Ia Protein Stability and Function," Diabetes 53: 3226-3232 (2004).
Cheeseright, "The Identification of Bioisosteres as Drug Development Candidates", Innovations in Pharmaceutical Technology, issue 28 (2009).
Cherng, "Synthesis of substituted pryidines by the reactions of halopyridines with sulfur,oxygen and carbon nucleophiles under focused microwave irradition", Tetrahedron, Jun. 10, 2002, 58(24): 4931-4935 (2002).
Clinicaltrials.gov: archive: NCT01235936 Nn Sep. 30, 2012[online]. U.S. National Institute of Health, Aug. 30, 2012; retrieved from the internet at <http:clinicaltrials.gov/archive/NCT01235936/2012_09_30> (Aug. 30, 2012).
Cousins, "Retina Today", 2 pages; retrieved from the internet at http://retinatoday.com/2009/10/1009_12.php (Oct. 2009).
Costello et al., "Evidence for changes in RREB-1, ZIP3, and zinc in the early development of pancreatic adenocarcinoma", J Gastrointest Canc, 43: 570-578 (2012).
Cunliffe et al., "Novel Inhibitors of Prolyl4-Hydroxylase. 3. Inhibition by the Substrate Analoe:ue N-Oxaloglycine and Its Derivatives," J. Med. Chem. 35: 2652-2658 (1992).

Demetriades et al., "Dynamic combinatorial chemistry employing embryonic boronic acids/boronate esters leads to potent oxygenase inhibitors", Angewandte Chemie, International Edition, Mav 25, 2012, 51(27): 6672-6675 (2012).
Designation of Inventors filed on entry into EP Regional Phase of EP Pat. No. 2044005.
Dranoff, "GM-CSP-secreting melanoma vaccines", Oncogene, 22: 3188-3192 (2003).
Elson et al., "Induction of hypervascularity without leakage or inflammation in transgenic mice overexpressing hypoxia-inducible factor-1α," Genes & Dev., 15: 2520-2532 (2001).
Elvidge et al., "Concordant Regulation of Gene Expression by Hypoxia and 2-Oxoglutarate-dependent Dioxvgenase Inhibition", J. Biol. Chem., 281(22): 15215-15226 (2006).
Enoch et al., "ABC of wound healing. Non-surgical and drug treatments", BMJ, 332(7546):332:900-3 (2006).
European Patent Office, Interlocutory Decision in Opposition Proceedings dated May 3, 2013 for European Patent No. 2044005, 76 pages.
European Patent Office, Minutes of the Oral Proceedings Before the Opposition Division dated May 3, 2013 for European Patent No. 2044005, 6 pages.
Extract from USPTO patent assignment database regarding U.S. Appl. No. 11/821,936.
Favier et al., "HIF2α reduces growth rate but promotes angiogenesis in a mouse model of neuroblastoma", BMC Cancer, 7:139: 1-10 (2007).
Flower, "Modelling G-protein-coupled receptors fordrug design," Biochimica et Biophysica Acta, 1422: 207-234 (1999).
Folkman et al., "Tumor Angiogenesis," The Molecular Basis of Cancer, Mendelsohn et al., eds., W. B. Saunders, Chapter 10: 206-232 (1995).
Franklin et al., "Approaches to the Design of Anti-Fibrotic Drugs," Biochem. Soc. Trans., 19(4): 812-5 (Nov. 1991).
Gaunt, "Rational Design of Benzyl-Type Protecting Groups Allows Sequential Deprotection of Hvdroxyl Groups by Catalytic Hydrogenolysis", 63(13): 4172-4173 (1998).
Gavhane et al., "Solid tumors: Facts, challenges, and solutions", International Journal of Pharma Sciences and Research, 2(1): 1-12 (2011).
Goodford, "A Computational Procedure for Determining Energetically Favorable Binding Sites on Biologically Important Macromolecules," J. Med. Chem., 28(7): 849-857 (1985).
Goodsell et al., "Automated Docking of Substrates to Proteins by Simulated Annealing", Proteins: Structure, Function, and Genetics, 8: 195-202 (1990).
Greer et al., "The updated biology of hypoxia inducible factor", EMBO J. 31: 2448-2460 (2012).
Hardcastle et al., "Discovery of Potent Chromen-4-one Inhibitors of the DNA-Dependent Protein Kinase (DNA-PK) Using a Small-Molecule Library Approach", J. of Medicinal Chem., 48(24): 7829-7846 (2005).
Hoeksema et al., "Structure of Rubradirin", J. of American Chem. Society, 104(19): 5173-5181 (1982).
Hu et al., "Differential Roles of Hypoxia-Inducible Factor 1α (HIF-1α) and HIF-2α in Hypoxic Gene Regulation", Mol. Cell. Biol., 23: 9361-9374 (2003).
Ingersoll et al. "Hippuric Acid", Organic Syntheses, CV 2, 328; retrieved from the internet at <http:web.archive.org/web20020724l35719/http://orgsyn.org/orgsyn/prepContent.asp ?prep=cv2p032 8> on Mar. 11, 2010.
International Preliminary Report on Patentability dated Dec. 10, 2013 for PCT/US2012/40833.
International Preliminary Report on Patentability for PCT/US2012/040833, filed Jun. 5, 2012.
International Search Report dated Apr. 14, 2008 for PCT/US2007/014832.
International Search Report and Written Opinion dated Aug. 29, 2012 for PCT/US2012/40833.
International Search Report and Written Opinion dated Apr. 20, 2015 for PCT/US2015/12634.

(56) References Cited

OTHER PUBLICATIONS

International Union of Pure and Applied Chemistry, Glossary of Class Names of Organic Compounds and Reactive Intermediates Based on Structure, Pure & D Annl. Chem., 67(8/9): 1307-1375 (1995).
Ivan et al., "Biochemical purification and pharmacological inhibition of a mammalian prolyl hydroxylase acting on hypoxia-inducible factor," Proceedings of the National Academy of Science, 99(21): 13459-13464 (2002).
Ivan et al., "HIFα Targeted for VHL-Mediated Destruction by Proline Hydroxylation: Implications for 02 Sensing", Science, 292: 464-468 (2001).
Ivanisevic et al., "Uses of X-Ray Powder Diffraction in the Pharmaceutical Industry." Pharmaceutical Formulation & Quality. Aug./Sep. 2011: 30-33 (2011).
Iyoda et al., "Homocoupling of aryl halides using nickel(II) complex and zinc in the presence of Et4NI. An efficient method for the synthesis of biaryls and bipyridines", Bull. Chem. Soc. Jpn., 63(1): 80-87 (1990).
Jaakkola et al., "Targeting of HIF-α to the von Rippel-Lindau Ubiquitylation Complex by O2-Regulated Prolyl Hydroxylation," Science, 292: 468-472 (2001).
Jones et al., "Molecular Recognition of Receptor Sites Using a Genetic Algorithm with a Description of Desolvation", J. Mol. Biol., 245: 43-53 (1995).
Kaelin, "Proline Hydroxylation and Gene Expression," Annual Rev. Biochem., 74: 115-125 (2005).
Karuppagounder et. al., "Hypoxia-inducible factor prolyl hydroxylase inhibition: robust new target or another big bust for stroke therapeutics?", J. Cereb. Blood F. Met., 32: 1347-1361 (2012).
Kawashima et al., "Suppressive effect of quinolinic acid and hippuric acid on bone marrow erythroid growth and lymphocyte blast formation in uremia", Advances in Experimental Medicine and Biology, 223: 69-72 (1987).
Ke and Costa, "Hypoxia-Inducible Factor-I (HIF-1)", Molecular Pharmacology, 70(5): 1469-1480 (2006).
Khandhadia et al., "Neurodegenerative Diseases", edited by Shamim I. Alnned, Published by Landes Biosciences and Springer Science+ Business Media, Chapter 2: 15-36 (2012).
Kietzmann et al., "Perivenous expression of the mRNA of the three hypoxia-inducible factor a-subunits, HIF1α, HIF2α, and HIF3α, in rat liver", Biochem. J., 354: 531-537 (2001).
Kim et al., "Recent advances in developing inhibitors for hypoxia-inducible factor prolyl hydroxylases and their therapeutic implications", Molecules, 20: 20551-20568 (2015).
Krantz, "Erythropoietin," Blood, 77: 419-434 (1991).
Kuntz et al., "A Geometric Approach to Macromolecule-Ligand Interactions," J. Mol. Biol., 161: 269-288 (1982).
Kurti et al., "Strategic applications of named reactions in organic synthesis", El Sevior: 448-449 and 484-485 (2005).
Langsetmo et al., "Inhibition of HIF-Prolyl Hydroxylases with FG-4539 Is Neuroprotective in a Mouse Model of Permanent Focal Ischemia", International Stroke Conference, Kissimmee Florida, Presentation No. 427 (2006).
Lee et al., "Structure of Human FIH-1 Reveals a Unique Active Site Pocket and Interaction Sites for HIF-1 and von Hippel Lindau", JBC, 278: 7558-7563 (2003).
Li et al., "PR39, A Peptide Regulator of Angiogenesis," Nat Med., 6(1): 49-55 (2000).
Lima and Barreiro, "Bioisosterism: A Useful Strategy for Molecular Modification and Drug Design", Current Medicinal Chemistry, 12: 23-49 (2005).
Liu et al., "Hypoxia Induces Genomic DNA Demethylation through the Activation of HIF-1alpha and Transcriptional Upregulation of MAT2A in Hepatoma Cells", Mol. Cancer Ther., 10: 1113-1123 (Jun. 2011).
Mancini et al., "Effect of Erythropoietin on Exercise Capacity in Patients with Moderate to Severe Chronic Heart Failure", Circulation, 107: 294-299 (2003).
McDonough et al., "Cellular Oxygen Sensing: Crystal Structure of Hypoxia-Inducible Factor Prolyl Hydroxylase (PHD2)", PNAS, 103(26): 9814-9819 (2006).
Miranker et al., "Functionality Maps of Binding Sites: A Multiple Copy Simultaneous Search Method", Proteins: Structure, Function and Genetics, 11: 29-34 (1991).
Morissette et al., "High-throughput crystallization: polymorphs, salts, co-crystals and solvates of pharmaceutical solids", Advanced Drug Delivery Reviews, 56: 275-300 (2004).
Myerson, Handbook of Industrial Crystallization, p. 249 (2002).
Nielsen et. al., "Antiangiogenic therapy for Breast Cancer", Breast Cancer Res. 12: 209-227 (2010).
Nguyen et al., "Cellular Interactions in Vascular Growth and Differentiation", Int. Review of Cytology, 204: 1-48 (2001).
Nishibata et al., "Automatic Creation of Drug Candidate Structures Based on Receptor Structure. Starting Point for Artificial Lead Generation", Tetrahedron, 47(43): 8985-8990 (1991).
Nowak et al., "Age-related macular degeneration (AMD): pathogenesis and therapy", Pharmacological Reports, 58: 353-363 (2006).
O'Reilly et al., "Angiostatin: A Novel Angiogenesis Inhibitor that Mediates the Suppression of Metastases by a Lewis Lung Carcinoma", Cell, 79: 315-328 (1994).
O'Reilly et al., "Endostatin: An Endogenous Inhibitor of Angiogenesis and Tumor Growth", Cell, 88: 277-285 (1997).
Online Abstract showing publication date of McDonough et al. as Jun. 16, 2006 (2006).
Pasqualetti et al., "Circadian rhythm of serum erythropoietin in myelodysplastic syndromes", European Review for Medical and Pharmacological Sciences, 4: 111-115 (2000).
PCT Request Form dated Jun. 26, 2007 for PCT/US2007/014832.
Pergola et al, "Vadadustat, a novel oral HIF stabilizer, provides effective anemia treatment in nondialysis-dependent chronic kidney disease", 90: 1115-1122 (2016).
Peyssonnaux et al., "HIF-1α Expression Regulates the Bactericidal Capacity of Phagocytes", J. Clinical Invest., 115(7): 1806-1815 (2005).
Piyamongkol et al., "Amido-3-hydroxypyridin-4-ones as Iron (III) Ligands", Chemistry A European Journal, 16: 6374-6381 (2010).
Prabhakar et. al., "Adaptive and Maladaptive Cardiorespiratory Responses to Continuous and Intermittent Hypoxia Mediated by Hypoxia-Inducible Factors 1 and 2", Physiol. Rev., 92: 967-1003 (2012).
PubChem Open Chemistry Database Compound Name: SCHEMBL3484399 (CID 49848485); Retrieved on from the internet: <https://pubchem.ncbi.nlm.nih.gov/compound/49848485> on Mar. 15, 2016.
PubChem Open Chemistry Database Compound Name: ZEADCOHJERWFOI-UHFFFAOYSA-M (CID 71491828); retrieved from the internet: <https://pubchem.ncbi.nlm.nih.gov/compound/71491828> on Mar. 21, 2016.
Qian et al., "A Randomized, Double-Blind, Placebo Controlled Trial of FG-4592 for Correction of Anemia in Subjects with Chronic Kidney Disease in China," Oral Abstract FR-ORO11, J. Am. Soc. Nephrol., 24: 38A (2013).
Qunibi et al., "A randomized controlled trial comparing intravenous ferric carboxymaltose with oral iron for treatment of iron deficiency of non-dialysis-dependent chronic kidney disease patients", Nephrol Dial Transplant, 26(5): 1599-1607 (2011).
Rahtu-Korpela et al., "HIF Prolyl 4-Hydroxylase-2 Inhibition Improves Glucose and Lipid Metabolism and Protects Against Obesity and Metabolic Dysfunction," Diabetes 63: 3324-3333 (2014).
Rankin et. al., "Hypoxia-inducible factor-2 (HIF-2) regulates hepatic erythropoietin in vivo" J. Clin. Invest. 117:1069-1076 (2007).
Ratcliffe et al., "HIF-1 and HIF-2: working alone or together in hypoxia?" J. Clin. Inv., 117(4):862-865 (2007).
Redondo et al., "Vascular endothelial growth factor (VEGF) and melanoma. N-Acetylcysteine downregulates VEGF production in vitro", Cytokine, 12(4):374-378 (2000).
Request for Correction of Inventorship at USPTO regarding U.S. Appl. 11/821,936.
Roda et al., "Stabilization of HIF-2α induces sVEGFR-1 production from tumor-associated macrophages and decreases tumor growth in a murine melanoma model", J. Immunology, 189: 3168-3177 (2012).

(56) References Cited

OTHER PUBLICATIONS

Schelhass and Waldmann, "Protecting Group Strategies in Organic Synthesis", Chem. Int. Ed. Engl., 36: 2056-2083 (1996).
Schoneberg et al., "Structural Basis of G Protein-Coupled Receptor Function," Molecular and Cellular Endocrinology, 151: 181-193 (1999).
Search Report dated Apr. 28, 2011 for European Pat. App. No. 11000872.9.
Semenza et al., "Transcriptional Regulation of Genes Encoding Glycolytic Enzymes by Hypoxia-Inducible Factor I", J. Biol. Chem., 269: 23757-23763 (1994).
Semenza et al., "Regulation of Erythropoietin Production: New Insights into Molecular Mechanisms of Oxygen Homeostasis", Hematol. Oncol. Clin. North Am., 8: 863-884 (1994).
Semenza, "HIF-1 and human disease: one highly involved factor", Genes & Development,14: 1983-1991 (2000).
Semenza, "Signal Transduction to Hypoxia-inducible Factor I", Biochem. Pharrnacol, 64: 993-998 (2002).
Sexton, "Recent advances in our understanding of peptide hormone receptors and RAMPS", Current Opinion in Drug Discovery and Development, 2(5): 440-448 (1999).
Seymour et al., "Decision T 0777/08 of the Boards of Appeal of the European Patent Office", retrieved from the internet: <http://www.epo.org/law-practice/case-law-appeals/pdf/1080777exl.pdf> on Dec. 19, 2017 (2011).
Sheehan, "3-Hydroxypicolinic Acid and Some of its Derivatives", J. Organic Chemistry 31(3): 636-638 (1996).
Siddiq, "Hypoxia-inducible factor prolyl 4-hydroxylase inhibition", J. of Biological Chemistry, 280(50):41732-41743 (2005).
Sowter et al., "Predominant Role of Hypoxia-Inducible Transcription Factor (Hif)-1α versus (Hif)-2α in Regulation of the Transcriptional Response to Hypoxia", Cancer Res. 63: 6130-6134 (2003).
Sporn and Suh, "Chemoprevention of cancer", Carcinogenesis, 21(3): 525-530(2000).
Stille, J. K., Angew. Chem., Int. ED. Engl., vol. 25: 508 (1986).
Stohlawetz et al., "Effects of erythropoietin on platelet reactivity and thrombopoiesis in humans", Blood, 95(9): 2983-2989 (2000).
Sutter, "Hypoxia-inducible factor 1 alpha protein expression is controlled by oxygen-regulated ubiquitination that is disrupted by deletions and missense mutations", PNAS, 97(9): 4748-4753 (2000).
Teicher et al., "Potentiation of Cytotoxic Cancer Therapies by TNP-470 Alone and with Other Anti-Angiogenic Agents", Int. J. Cancer, 57: 920-925 (1994).
Thornber, "Isosterism and Molecular Modification in Drug Design", Progress Drug Res., vol. 37: 563-580 (1979).
Thoppil and Bishayee, "Terpenoids as potential chemopreventive and therapeutic agents in liver cancer", World J. Hepatol., 3(9): 228-249 (2011).
Tzschucke et al., "Fluorous-Silica-Supported Perfluoro-Tagged Palladium Complexes Catalyze Suzuki Coupling in Water", Helvetica Chimica Acta; 87: 2882-2889 (2004).
Ullmann F., J. Bielecki, Ber. Deutsch. Chem. Ges. 1901, p. 2174, 34. (1901).
Variankaval et al., "From form to function: crystallization of active pharmaceutical ingredients", AICHE Journal, Jul. 2008, 54(7): 1682-1688 (2008).
Vickerstaffe et al., "Fully Automated Polymer-Assisted Synthesis of 1,5-Biaryl Pvrazoles", J. Comb. Chem., 6:332-33 (2004).
Vincent et al., "Angiogenesis is Induced in a Rabbit Model of Hindlimb Ischemia by Naked DNA Encoding an HIF-1α/VP16 Hybrid Transcription Factor", Circulation, 102: 2255-2261 (2000).
Vippagunta et al., "Crystalline solids", Adv. Drug Deliv. Rev., 48(1): 3-26 (2001).
Wade et al., "Organic Chemistry", 6th ED., Pearson Prentice Hall, US: 780-781 (2006).
Warnecke et al., "Activation of the Hypoxia-Inducible Factor Pathway and Stimulation of Angiogenesis by Application of Prolyl Hydroxylase Inhibitors", FASEB Journal, 17: 1186-1188 (2003).
Warshakoon et al., "Design and synthesis of substituted pyridine derivatives as HIF-1alpha prolyl hydroxylase inhibitors", Bioorganic & Medicinal Chemistry Letters, 16: 5616-5620 (2006).
Wax et al., "SM-20 is a Novel20-kd Protein Whose Expression in the Arterial Wall is Restricted to Smooth Muscle", Lab. Invest., 74(4): 797-808 (1996).
Weidner et al., "Tumor Angiogenesis and Metastasis—Correlation in Invasive Breast Carcinoma", New Eng. J. Med., 324(1): 1-8 (1991).
Wiesener et al., "Widespread hypoxia-inducible expression of HIF-2alpha in distinct cell populations of different organs." FASEB J.17(2): 271-3 (2003).
Wright et al., "Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes", J. Bio. Chem., 278(22): 20235-20239 (2003).
Wu et. al., "A systems biology perspective on sVEGFR1: its biological function, pathogenic role and therapeutic use", J. Cell. Mol. Med. 14:528-552 (2010).
Yang et al., "Desmoplakin acts as a tumor suppressor by inhibition of the Wnt/beta-catenin signaling pathway in human lung cancer", Carcinogenesis, 33(10): 1863-1870 (2012).
CAS Registry Nos. 1261773-17-4, 1261723-73-2. Chemcats, 2 pages (2011).
CAS Registry Nos. 1361809-77-9, 1361737-20-3, 1361721-11-0, 1361693-45-9, 1361676-79-0. Chemcats, 5 pages (2012).
CAS Registry Nos. 1361609-40-6, 1361556-21-9, 1361555-42-1, 1361544-77-5, 1361480-63-8, 1361477-92-0. Chemcats, 6 pages (2012).

PROCESS FOR PREPARING [(3-HYDROXYPYRIDINE-2-CARBONYL) AMINO]ALKANOIC ACIDS, ESTERS AND AMIDES

PRIORITY

This application is a continuation of U.S. application Ser. No. 16/352,705, filed Mar. 13, 2019, which is a continuation of U.S. application Ser. No. 15/692,255, filed Aug. 31, 2017, now U.S. Pat. No. 10,246,416, which is a continuation of U.S. application Ser. No. 14/833,222, filed Aug. 24, 2015, now U.S. Pat. No. 9,776,969, which is a divisional of U.S. application Ser. No. 13/488,554, filed Jun. 5, 2012, now U.S. Pat. No. 9,145,366, which claims the benefit of U.S. Provisional Application No. 61/493,536, filed Jun. 6, 2011, the entirety of each of which are included herein by reference.

FIELD

Disclosed are processes for preparing [(3-hydroxypyridine-2-carbonyl)amino]-alkanoic acids, derivatives, inter alia, 5-aryl substituted and 5-heteroaryl substituted [(3-hydroxypyridine-2-carbonyl]amino}acetic acids. Further disclosed are methods for making prodrugs of [(3-hydroxypyridine-2-carbonyl)-amino]acetic acids, for example, [(3-hydroxypyridine-2-carbonyl]amino}acetic acid esters and {[3-hydroxypyridine-2-carbonyl]amino}acetic acid amides. The disclosed compounds are useful as prolyl hydroxylase inhibitors or for treating conditions wherein prolyl hydroxylase inhibition is desired.

DETAILED DISCLOSURE

Figure 1:
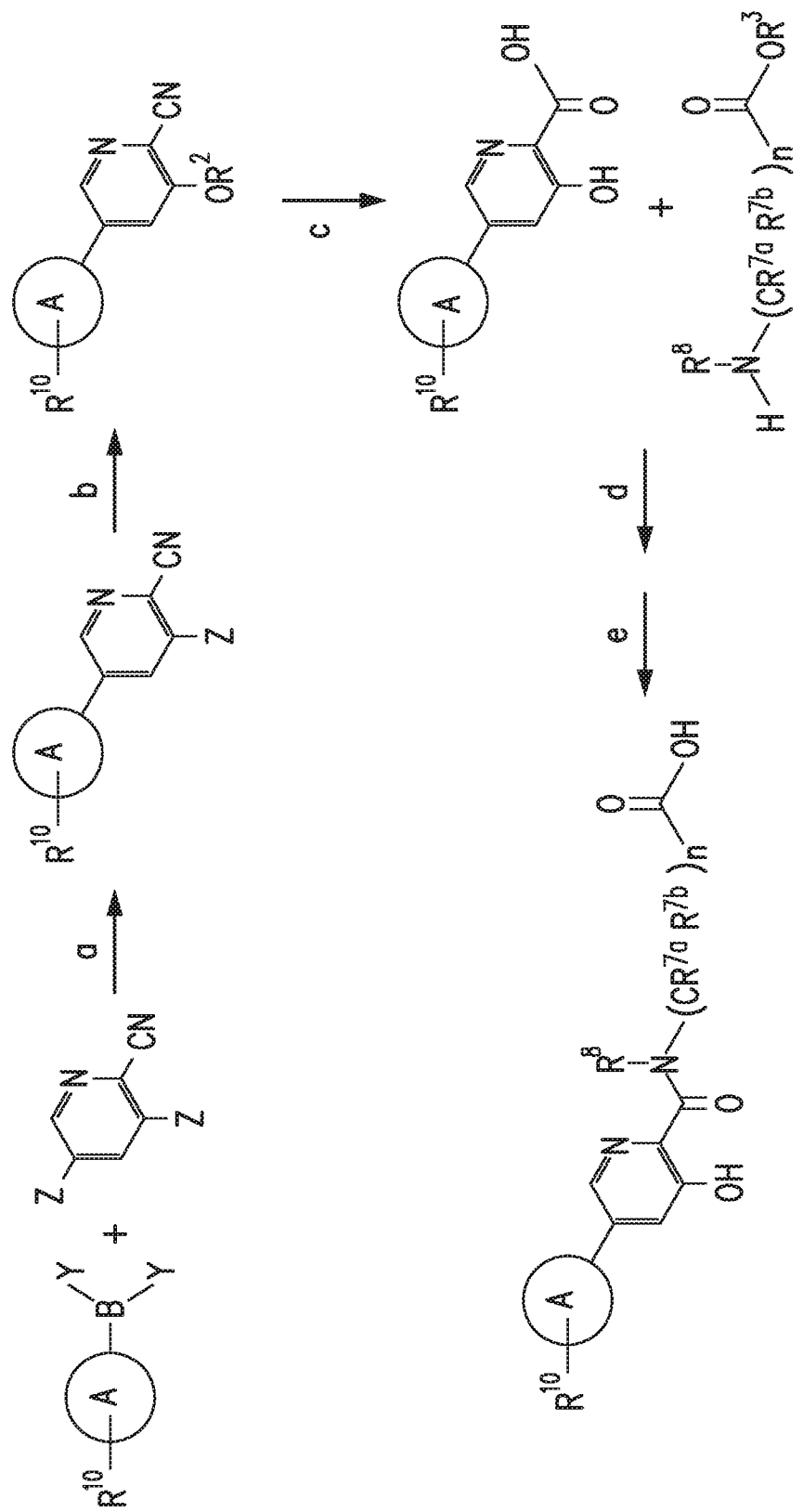
FIG. 1 depicts an outline of one embodiment for preparing the disclosed prolyl hydroxylase inhibitors.
Figure 2:
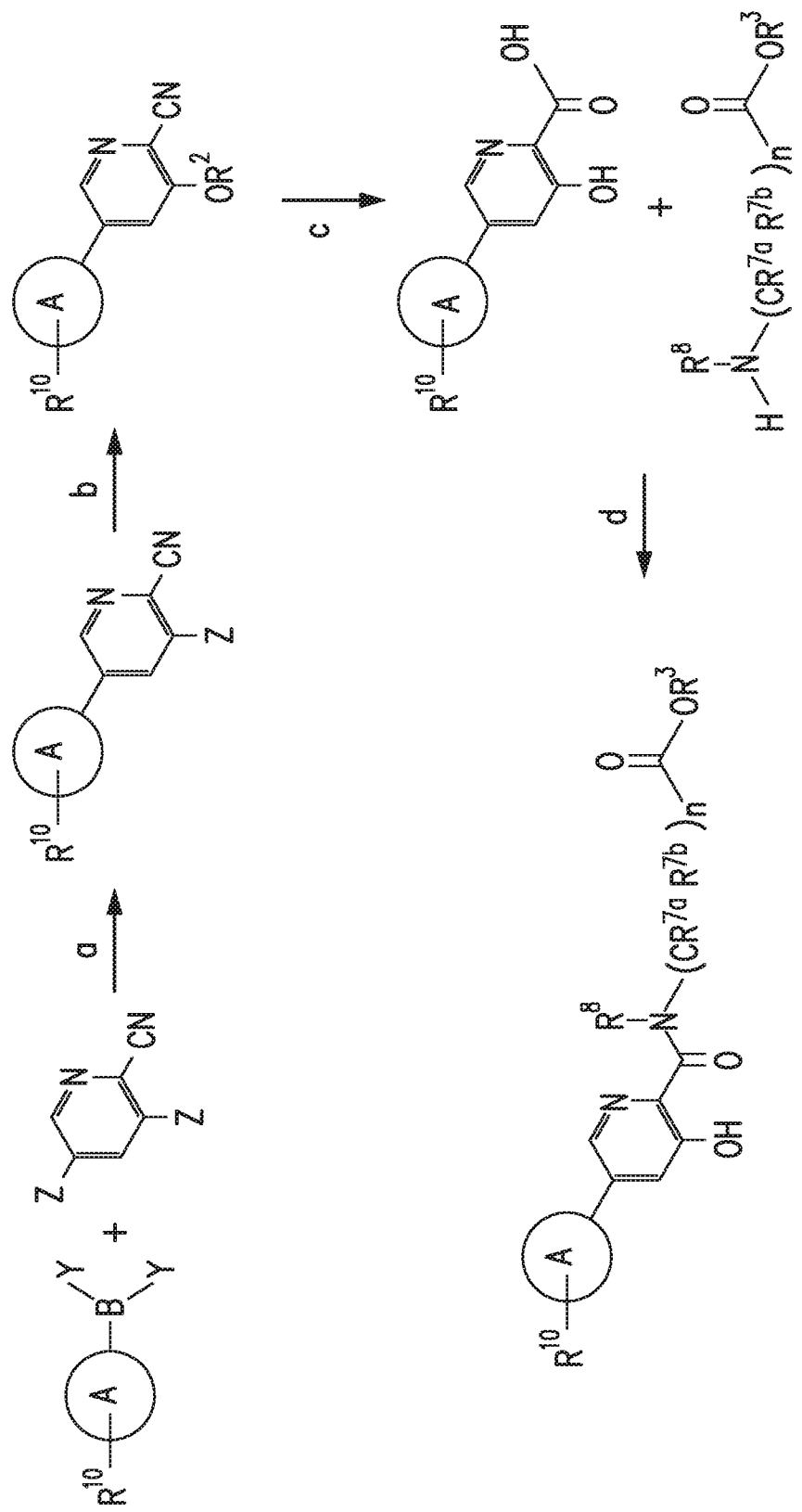
FIG. 2 depicts an outline of one embodiment for preparing the disclosed prolyl hydroxylase inhibitor ester prodrugs.
Figure 3:
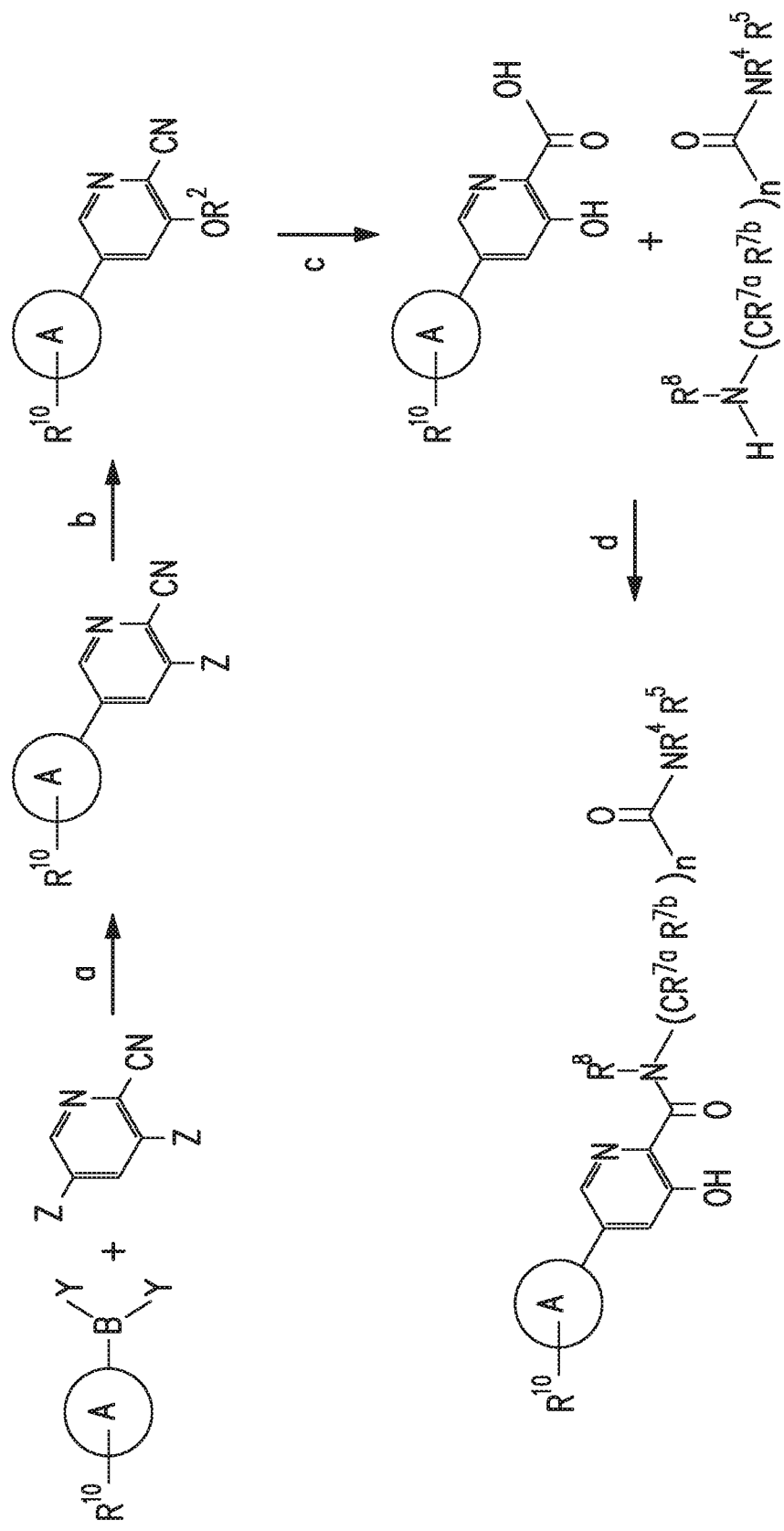
FIG. 3 depicts an outline of one embodiment for preparing the disclosed prolyl hydroxylase inhibitor amide prodrugs.

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

A weight percent of a component, unless specifically stated to the contrary, is based on the total weight of the formulation or composition in which the component is included.

"Admixture" or "blend" is generally used herein means a physical combination of two or more different components.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "[(3-hydroxypyridine-2-carbonyl) amino]alkanoic acid" includes mixtures of two or more such [(3-hydroxypyridine-2-carbonyl)amino]alkanoic acids, reference to "the compound" includes mixtures of two or more such compounds, which can include mixtures of optical isomers (racemic mixtures), and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (i.e., carbocyclic and aryl rings) or these units can comprise one or more heteroatoms in the ring (i.e., heterocyclic and heteroaryl rings). For "carbocyclic" rings the lowest number of carbon atoms in a ring is 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl, a $C_1$ heterocyclic ring. Ethylene oxide comprises 2 carbon atoms and is a $C_2$ heterocyclic ring. For "heteroaryl" rings the lowest number of carbon atoms in a ring is 1 carbon atom; 1,2,3,4-tetrazolyl, a $C_1$ heteroaryl ring. The terms "heterocycle" and "heterocyclic ring" can also include "heteroaryl rings." The following is a non-limiting description of the units encompassed by the terms "acyclic hydrocarbyl" and "cyclic hydrocarbyl" as used herein.

A. Substituted and unsubstituted acyclic hydrocarbyl:

For the purposes of the present disclosure the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and unsubstituted cyclic hydrocarbyl:

For the purposes of the present disclosure the term "substituted and unsubstituted cyclic hydrocarbyl" encompasses 5 categories of units:

1) The term "carbocyclic" is defined herein as "encompassing rings comprising from 3 to 20 carbon atoms, in one embodiment from 3 to 10 carbon atoms, in another embodiment from 3 to 7 carbon atoms, in a still further embodiment 5 or 6 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

ii) $C_6$ or $C_{10}$ aryl rings fused with 1 or 2 saturated rings to afford $C_5$-$C_{20}$ ring systems, non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which contains the heteroatom is also not an aromatic ring." The following are non-limiting examples of "substituted and unsubstituted heterocyclic rings" which encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl (C$_4$), piperidinyl (C$_4$), dihydropyranyl (C$_5$), tetrahydropyranyl (C$_5$), piperidin-2-onyl (valerolactam) (C$_5$), 2,3,4,5-tetrahydro-1H-azepinyl (C$_6$), 2,3-dihydro-1H-indole (C$_8$), and 1,2,3,4-tetrahydroquinoline (C$_9$).

ii) heterocyclic units having 2 or more rings one of which is a heterocyclic ring, non-limiting examples of which include hexahydro-1H-pyrrolizinyl (C$_7$), 3a,4,5,6,7,7a-hexahydro-1H-benzo[d]imidazolyl (C$_7$), 3a,4,5,6,7,7a-hexahydro-1H-indolyl (C$_8$), 1,2,3,4-tetrahydroquinolinyl (C$_9$), and decahydro-1H-cycloocta[b]pyrrolyl (C$_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." Heteroaryl rings can comprise from 1 to 19 carbon atoms, in another embodiment heteroaryl rings can comprise from 1 to 9 carbon atoms. The following are non-limiting examples of "substituted and unsubstituted heterocyclic rings" which encompass the following categories of units:

i) heteroaryl rings containing a single ring, non-limiting examples of which include, 1,2,3,4-tetrazolyl (C$_1$), [1,2,3]triazolyl (C$_2$), [1,2,4]triazolyl (C$_2$), triazinyl (C$_3$), thiazolyl (C$_3$), 1H-imidazolyl (C$_3$), oxazolyl (C$_3$), isoxazolyl (C$_3$), isothiazolyl (C$_3$), furanyl (C$_4$), thiophenyl (C$_4$), pyrimidinyl (C$_4$), 2-phenylpyrimidinyl (C$_4$), pyridinyl (C$_5$), 3-methylpyridinyl (C$_5$), and 4-dimethylaminopyridinyl (C$_5$).

ii) heteroaryl rings containing 2 or more fused rings one of which is a heteroaryl ring, non-limiting examples of which include: 7H-purinyl (C$_5$), 9H-purinyl (C$_5$), 6-amino-9H-purinyl (C$_5$), 5H-pyrrolo[3,2-d]pyrimidinyl (C$_6$), 7H-pyrrolo[2,3-d]pyrimidinyl (C$_6$), pyrido[2,3-d]pyrimidinyl (C$_7$), 2-phenylbenzo[d]thiazolyl (C$_7$), 1H-indolyl (C$_8$), 4,5,6,7-tetrahydro-1-H-indolyl (C$_8$), quinoxalinyl (C$_8$), 5-methylquinoxalinyl (C$_8$), quinazolinyl (C$_8$), quinolinyl (C$_9$), 8-hydroxy-quinolinyl (C$_9$), and isoquinolinyl (C$_9$).

5) C$_1$-C$_6$ tethered cyclic hydrocarbyl units (whether carbocyclic units, C$_6$ or C$_{10}$ aryl units, heterocyclic units, or heteroaryl units) which connected to another moiety, unit, or core of the molecule by way of a C$_1$-C$_6$ alkylene unit. Non-limiting examples of tethered cyclic hydrocarbyl units include benzyl C$_1$-(C$_6$) having the formula:

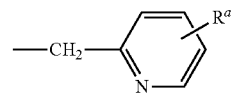

wherein R$^a$ is optionally one or more independently chosen substitutions for hydrogen. Further examples include other aryl units, inter alia, (2-hydroxyphenyl)hexyl C$_6$-(C$_6$); naphthalen-2-ylmethyl C$_1$-(C$_{10}$), 4-fluorobenzyl C$_1$-(C$_6$), 2-(3-hydroxyphenyl)ethyl C$_2$-(C$_6$), as well as substituted and unsubstituted C$_3$-C$_{10}$ alkylenecarbocyclic units, for example, cyclopropylmethyl C$_1$-(C$_3$), cyclopentylethyl C$_2$-(C$_5$), cyclohexylmethyl C$_1$-(C$_6$). Included within this category are substituted and unsubstituted C$_1$-C$_{10}$ alkylene-heteroaryl units, for example a 2-picolyl C$_1$-(C$_6$) unit having the formula:

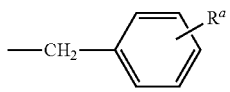

wherein R$^a$ is the same as defined above. In addition, C$_1$-C$_{12}$ tethered cyclic hydrocarbyl units include C$_1$-C$_{10}$ alkyleneheterocyclic units and alkylene-heteroaryl units, non-limiting examples of which include, aziridinylmethyl C$_1$-(C$_2$) and oxazol-2-ylmethyl C$_1$-(C$_3$).

For the purposes of the present disclosure carbocyclic rings are from C$_3$ to C$_{20}$; aryl rings are C$_6$ or C$_{10}$; heterocyclic rings are from C$_1$ to C$_9$; and heteroaryl rings are from C$_1$ to C$_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

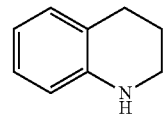

is, for the purposes of the present disclosure, defined as a heterocyclic unit. 6,7-Dihydro-5H-cyclopentapyrimidine having the formula:

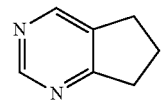

is, for the purposes of the present disclosure, is defined as a heteroaryl unit. When a fused ring unit contains heteroatoms in both a non-aromatic ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthpyridine having the formula:

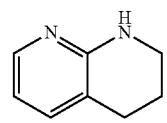

is, for the purposes of the present disclosure, is defined as a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) substituted or unsubstituted $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_7$ or $C_{11}$ alkylenearyl; for example, benzyl, 2-phenylethyl, naphthylen-2-ylmethyl;

iv) substituted or unsubstituted $C_1$-$C_9$ heterocyclic rings; as described herein below;

v) substituted or unsubstituted $C_1$-$C_9$ heteroaryl rings; as described herein below;

vi) —$(CR^{102a}R^{102b})_aOR^{101}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —$(CR^{102a}R^{102b})_aC(O)R^{101}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;

viii) —$(CR^{102a}R^{102b})_aC(O)OR^{101}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

ix) —$(CR^{102a}R^{102b})_aC(O)N(R^{101})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{102a}R^{102b})_aN(R^{101})C(O)R^{101}$; for example, —$NHCOCH_3$, —$CH_2NHCOCH_3$, —$NHCOCH_2CH_3$, and —$CH_2NHCOCH_2CH_3$;

xi) —$(CR^{102a}R^{102b})_aN(R^{101})$ $C(O)_2R^{101}$; for example, —$NHCO_2CH_3$, —$CH_2NHCO_2CH_3$, —$NHCO_2CH_2CH_3$, and —$CH_2NHCO_2CH_2CH_3$;

xii) —$(CR^{102a}R^{102b})_aN(R^{101})_2$; for example, —$NH_2$, —$CH_2NH_2$, —$NHCH_3$, —$CH_2NHCH_3$, —$N(CH_3)_2$, and —$CH_2N(CH_3)_2$;

xiii) halogen; —F, —Cl, —Br, and —I;

xiv) —$(CR^{102a}R^{102b})_aCN$;

xv) —$(CR^{102a}R^{102b})_aNO_2$;

xvi) —$(CH_jX_k)_aCH_{j'}X_{k'}$; wherein X is halogen, the index j is an integer from 0 to 2, j+k=3; the index j' is an integer from 0 to 2, j'+k'=2; for example, —$CH_2F$, —$CHF_2$, —$CH_2CH_2F$, —$CH_2CHF_2$, —$CF_3$, —$CCl_3$, or —$CBr_3$;

xvii) —$(CR^{102a}R^{102b})_aSR^{101}$; —SH, —$CH_2SH$, —$SCH_3$, —$CH_2SCH_3$, —$SC_6H_5$, and —$CH_2SC_6H_5$;

xviii) —$(CR^{102a}R^{102b})_aSO_2R^{101}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and xix) —$(CR^{102a}R^{102b})_aSO_3R^{101}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{101}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or $C_3$-$C_4$ branched alkyl; the index "a" is from 0 to 4.

The substitutions for hydrogen defined herein above, for example, substituted $C_1$-$C_{12}$ linear, $C_3$-$C_{12}$ branched, or $C_3$-$C_{12}$ cyclic alkyl, alkenyl, and alkynyl, substituted $C_6$ or $C_{10}$ aryl, substituted $C_7$ or $C_{11}$ alkylenearyl, substituted $C_1$-$C_9$ heterocyclic rings, substituted $C_1$-$C_9$ heteroaryl rings, and $R^{101}$, can be optionally substituted by one or more of the following substitutions for hydrogen:

i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) $C_6$ or $C_{10}$ aryl; for example, phenyl, naphthyl (also referred to herein as naphthylen-1-yl ($C_{10}$) or naphthylen-2-yl ($C_{10}$));

iii) $C_7$ or $C_{11}$ alkylenearyl; for example, benzyl, 2-phenylethyl, naphthylen-2-ylmethyl;

iv) $C_1$-$C_9$ heterocyclic rings; as described herein below;

v) $C_1$-$C_9$ heteroaryl rings; as described herein below;

vi) —$(CR^{202a}R^{202b})_bOR^{201}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —$(CR^{202a}R^{202b})_bC(O)R^{201}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;

viii) —$(CR^{202a}R^{202b})_bC(O)OR^{201}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

ix) —$(CR^{202a}R^{202b})_bC(O)N(R^{201})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{202a}R^{202b})_bN(R^{201})$ $C(O)R^{201}$; for example, —$NHCOCH_3$, —$CH_2NHCOCH_3$, —$NHCOCH_2CH_3$, and —$CH_2NHCOCH_2CH_3$;

xi) —(CR$^{202a}$R$^{202b}$)$_b$N(R$^2$) C(O)$_2$R$^{201}$; for example, —NHCO$_2$CH$_3$, —CH$_2$NHCO$_2$CH$_3$, —NHCO$_2$CH$_2$CH$_3$, and —CH$_2$NHCO$_2$CH$_2$CH$_3$;

xii) —(CR$^{202a}$R$^{202b}$)$_b$N(R$^{201}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;

xiii) halogen; —F, —Cl, —Br, and —I;

xiv) —(CR$^{202a}$R$^{202b}$)$_b$CN;

xv) —(CR$^{202a}$R$^{202b}$)$_b$NO$_2$;

xvi) —(CH$_j$X$_k$)$_a$CH$_{j'}$X$_{k'}$; wherein X is halogen, the index j is an integer from 0 to 2, j+k=3; the index j' is an integer from 0 to 2, j'+k'=2; for example, —CH$_2$F, —CHF$_2$, —CH$_2$CH$_2$F, —CH$_2$CHF$_2$, —CF$_3$, —CCl$_3$, or —CBr$_3$;

xvii) —(CR$^{202a}$R$^{202b}$)$_b$SR$^{201}$; —SH, —CH$_2$SH, —SCH$_3$, —CH$_2$SCH$_3$, —SC$_6$H$_5$, and —CH$_2$SC$_6$H$_5$;

xviii) —(CR$^{202a}$R$^{202b}$)$_b$SO$_2$R$^{201}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xix) —(CR$^{202a}$R$^{202b}$)$_b$SO$_3$R$^{201}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{201}$ is independently hydrogen, C$_1$-C$_6$ linear, C$_3$-C$_6$ branched, or C$_3$-C$_6$ cyclic alkyl, phenyl, benzyl, heterocyclic, or heteroaryl; or two R$^{201}$ units can be taken together to form a ring comprising 3-7 atoms; R$^{202a}$ and R$^{202b}$ are each independently hydrogen or C$_1$-C$_4$ linear or C$_3$-C$_4$ branched alkyl; the index "b" is from 0 to 4.

For the purposes of the present disclosure the terms "compound," "analog," and "composition of matter" stand equally well for each other and are used interchangeably throughout the specification. The disclosed compounds include all enantiomeric forms, diastereomeric forms, salts, and the like.

The compounds disclosed herein include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, tromethamine, meglumine and the like.

The disclosed process can be used to prepare compounds having the formula:

wherein R and R$^1$ are further defined herein.

Compounds having the formula:

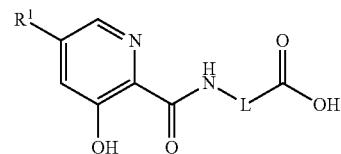

wherein L is a linking group defined herein, have been found to exhibit prolyl hydroxylase inhibition (antagonism). Compounds of this formula have also been found to stabilize hypoxia inducible factor-2 alpha (HIF-2a). It has also been found that esters and amides having the formula:

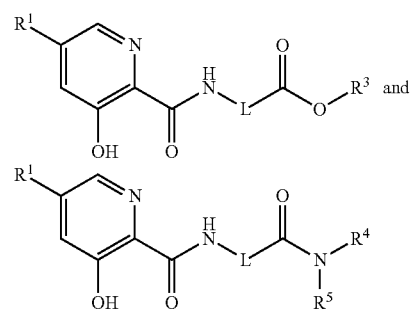

can hydrolyze in vivo, in vitro and ex vivo to the corresponding carboxylic acids shown above. As such, these esters and amides are referred to herein as "prodrugs."

R Units

R units have the formula:

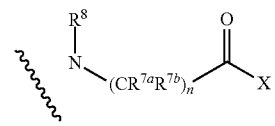

wherein X is chosen from:
i) —OH;
ii) —OR$^3$;
iii) —NR$^4$R$^5$; and
iv) —OM$^1$.

R$^3$ is C$_1$-C$_{12}$ linear, C$_3$-C$_{12}$ branched or C$_3$-C$_{12}$ cyclic alkyl; C$_2$-C$_{12}$ linear, C$_3$-C$_{12}$ branched or C$_3$-C$_{12}$ cyclic alkenyl; or C$_2$-C$_{12}$ linear, C$_3$-C$_{12}$ branched or C$_3$-C$_{12}$ cyclic alkynyl, or benzyl.

R$^4$ and R$^5$ are each independently hydrogen, C$_1$-C$_{12}$ linear, C$_3$-C$_{12}$ branched or C$_3$-C$_{12}$ cyclic alkyl; C$_2$-C$_{12}$ linear, C$_3$-C$_{12}$ branched or C$_3$-C$_{12}$ cyclic alkenyl; or C$_2$-C$_{12}$ linear, C$_3$-C$_{12}$ branched or C$_3$-C$_{12}$ cyclic alkynyl; benzyl; or R$^4$ and R$^5$ can be taken together with the nitrogen atom to form a 3 to 10 member ring, wherein the ring can optionally contain one or more heteroatoms chosen from oxygen (O), nitrogen (N), or sulfur (S). M$^1$ represents a cation as further described herein below.

When a ring is formed from R$^4$ and R$^5$ and the ring contains a ring nitrogen other than the nitrogen atom to which R$^4$ and R$^5$ are bonded, then the nitrogen atom can have the form —NR$^9$— or =N—, wherein R$^9$ can be hydrogen or methyl. Non-limiting examples of this embodiment includes compounds having the formula:

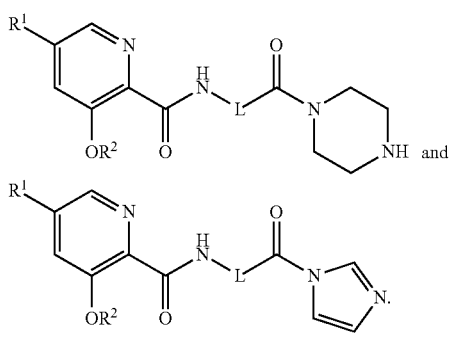

In one aspect, X is hydroxyl, —OH.

In a further aspect, X is —OR$^3$. One embodiment of this aspect relates to X units wherein R$^3$ is C$_1$-C$_6$ linear alkyl, for example, methyl (C$_1$), ethyl (C$_2$), n-propyl (C$_3$), n-butyl (C$_4$), n-pentyl (C$_5$), and n-hexyl (C$_6$). Non-limiting examples include the methyl ester, the ethyl ester, the n-propyl ester, and the like.

Another embodiment of this aspect relates to X units wherein R$^3$ is C$_3$-C$_6$ branched alkyl non-limiting examples of which include iso-propyl (C$_3$), sec-butyl (C$_4$), iso-butyl (C$_4$), tert-butyl (C$_4$), 1-methylbutyl (C$_5$), 2-methylbutyl (C$_5$), 3-methylbutyl (C$_5$), and 4-methylpentyl (C$_6$).

A further embodiment of this aspect relates to X units wherein R$^3$ is C$_3$-C$_6$ cyclic alkyl, for example, cyclopropyl (C$_3$), cyclobutyl (C$_4$), cyclopentyl (C$_5$), and cyclohexyl (C$_6$).

In another aspect, X is —NR$^4$R$^5$. One embodiment of this aspect relates to X units wherein R$^4$ and R$^5$ are both hydrogen; —NH$_2$.

A further embodiment of this aspect relates to X units wherein R$^4$ and R$^5$ are independently chosen from hydrogen, C$_1$-C$_4$ linear alkyl, C$_3$-C$_4$ branched alkyl, or C$_3$-C$_4$ cyclic alkyl, for example, methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$). Non-limiting examples of this embodiment include —NH$_2$, —NHCH$_3$, —N(CH$_3$)$_2$, —NHC$_2$H$_5$, —N(C$_2$H$_5$)$_2$, and —N(CH$_3$)(C$_2$H$_5$).

L is a linking unit having the formula —(CR$^{7a}$R$^{7b}$)$_n$— wherein R$^{7a}$ and R$^{7b}$ can be independently chosen from hydrogen, C$_1$-C$_6$ linear, C$_3$-C$_6$ branched or C$_3$-C$_6$ cyclic alkyl. The index n is an integer from 1 to 4.

In one aspect of L units, R$^{7a}$ and R$^{7b}$ are both hydrogen and the index n is an integer from 1 to 4, i.e., —CH$_2$— (methylene), —CH$_2$CH$_2$— (ethylene), —CH$_2$CH$_2$CH$_2$— (propylene), and —CH$_2$CH$_2$CH$_2$CH$_2$— (butylene). One iteration of L units according to this aspect relates to compounds having the formula:

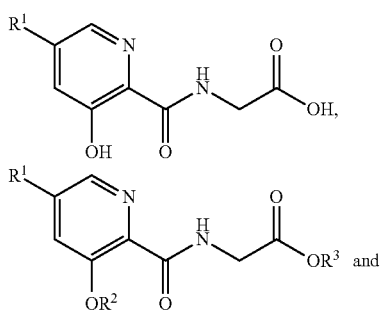

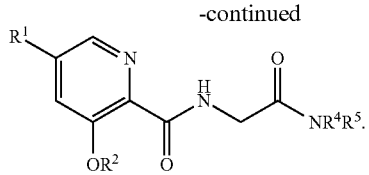

A further aspect of L units relates to L units wherein R$^{7a}$ and R$^{7b}$ are independently chosen from hydrogen, methyl (C$_1$), ethyl (C$_2$), n-propyl (C$_3$), and iso-propyl (C$_3$) and the index n is an integer from 1 to 4. One embodiment of this aspect relates to L units wherein R$^{7a}$ is hydrogen and R$^{7b}$ is chosen from methyl (C$_1$), ethyl (C$_2$), n-propyl (C$_3$), and iso-propyl (C$_3$), and the index n is an integer from 1 or 3. Non-limiting examples of this embodiment includes —CH(CH$_3$)—, —CH$_2$CH(CH$_3$)—, —CH(CH$_3$)CH$_2$—, —CH(CH$_3$)CH$_2$CH$_2$—, —CH$_2$CH(CH$_3$)CH$_2$—, and —CH$_2$CH$_2$CH(CH$_3$)—.

A yet further aspect of L units relates to L units wherein R$^{7a}$ and R$^{7b}$ are independently chosen from methyl (C$_1$), ethyl (C$_2$), n-propyl (C$_3$), and iso-propyl (C$_3$) and the index n is an integer from 1 to 4. A non-limiting example of this aspect has the formula —C(CH$_3$)$_2$—.

In a still further aspect of L units, L units can be derived from the reaction of an amino acid with a 5-aryl or 5-heteroaryl-3-hydroxy-2-carboxypyridine as described herein below in the disclosure of process step D. One embodiment of this aspect of L relates to L units wherein R$^{7b}$ is hydrogen and R$^{7a}$ is chosen from hydrogen, methyl, iso-propyl, iso-butyl, sec-butyl, hydroxymethyl, 1-hydroxyethyl, thiomethyl, 2-(methylthio)ethyl, benzyl, (4-hydroxyphenyl)methyl, indol-3-ylmethyl, imidazol-4-ylmethyl, 3-gunidinylpropyl, 4-aminobutyl, carboxymethyl, 2-carboxyethyl, acetamide, or R$^8$ and R$^{7a}$ can be taken together to form a pyrrolidinyl ring, for example, when proline is reacted with the 5-aryl or 5-heteroaryl-3-hydroxy-2-carboxypyridine.

The index n can be any integer from 1 to 4, for example n can equal 1, n can equal 2, n can equal 3, and n can equal 4.

R$^8$ is hydrogen, methyl (C$_1$) or ethyl (C$_2$). In one aspect R$^8$ is hydrogen. In a further aspect R$^8$ is methyl (C$_1$). In another aspect R$^8$ is ethyl (C$_2$).

R$^1$ Units

R$^1$ units are chosen from:
i) substituted or unsubstituted C$_6$ or C$_{10}$ aryl; and
ii) substituted or unsubstituted C$_1$-C$_9$ heteroaryl.
Non-limiting examples of substitutions for a hydrogen atom on R$^1$ units, or alternatively an R$^{10}$ unit when R$^1$ is represented by an A ring, include:
i) C$_1$-C$_{12}$ linear, C$_3$-C$_{12}$ branched, or C$_3$-C$_{12}$ cyclic alkyl, alkenyl, and alkynyl; for example, methyl (C$_1$), ethyl (C$_2$), ethenyl (C$_2$), ethynyl (C$_2$), n-propyl (C$_3$), iso-propyl (C$_3$), cyclopropyl (C$_3$), 3-propenyl (C$_3$), 1-propenyl (also 2-methylethenyl) (C$_3$), isopropenyl (also 2-methylethen-2-yl) (C$_3$), prop-2-ynyl (also propargyl) (C$_3$), propyn-1-yl (C$_3$), n-butyl (C$_4$), sec-butyl (C$_4$), iso-butyl (C$_4$), tert-butyl (C$_4$), cyclobutyl (C$_4$), buten-4-yl (C$_4$), cyclopentyl (C$_5$), cyclohexyl (C$_6$);
ii) C$_6$ or C$_{10}$ aryl; for example, phenyl, naphthyl (also referred to herein as naphthylen-1-yl (C$_{10}$) or naphthylen-2-yl (C$_{10}$));
iii) C$_7$ or C$_{11}$ alkylenearyl; for example, benzyl, 2-phenylethyl, naphthylen-2-ylmethyl;

iv) $C_1$-$C_9$ heterocyclic rings; as described herein below;
v) $C_1$-$C_9$ heteroaryl rings; as described herein below;
vi) —$(CR^{102a}R^{102b})_aOR^{101}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{102a}R^{102b})_aC(O)R^{101}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_3$;
viii) —$(CR^{102a}R^{102b})_aC(O)OR^{101}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
ix) —$(CR^{102a}R^{102b})_aC(O)N(R^{101})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{102a}R^{102b})_aN(R^{101})C(O)R^{101}$; for example, —$NHCOCH_3$, —$CH_2NHCOCH_3$, —$NHCOCH_2CH_3$, and —$CH_2NHCOCH_2CH_3$;
xi) —$(CR^{102a}R^{102b})_aN(R^{101})C(O)_2R^{11}$; for example, —$NHCO_2CH_3$, —$CH_2NHCO_2CH_3$, —$NHCO_2CH_2CH_3$, and —$CH_2NHCO_2CH_2CH_3$;
xii) —$(CR^{102a}R^{102b})_aN(R^{101})_2$; for example, —$NH_2$, —$CH_2NH_2$, —$NHCH_3$, —$CH_2NHCH_3$, —$N(CH_3)_2$, and —$CH_2N(CH_3)_2$;
xiii) halogen; —F, —Cl, —Br, and —I;
xiv) —$(CR^{102a}R^{102b})_aCN$;
xv) —$(CR^{102a}R^{102b})_aNO_2$;
xvi) —$(CH_jX_{k'})_aCH_jX_k$; wherein X is halogen, the index j is an integer from 0 to 2, j+k=3; the index j' is an integer from 0 to 2, j'+k'=2; for example, —$CH_2F$, —$CHF_2$, —$CF_3$, —$CCl_3$, or —$CBr_3$;
xvii) —$(CR^{102a}R^{102b})_aSR^{101}$; —SH, —$CH_2SH$, —$SCH_3$, —$CH_2SCH_3$, —$SC_6H_5$, and —$CH_2SC_6H_5$;
xviii) —$(CR^{102a}R^{102b})_aSO_2R^{101}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xix) —$(CR^{102a}R^{102b})_aSO_3R^{101}$; for example, —$SO_3H$, —$CH_2SO_3H$, —$SO_3CH_3$, —$CH_2SO_3CH_3$, —$SO_3C_6H_5$, and —$CH_2SO_3C_6H_5$; or
xx) two substitutions for hydrogen can be taken together to form a substituted or unsubstituted $C_2$-$C_8$ heterocyclic ring, wherein the ring substitution can be one or more of the substitutions defined in (i) to (xix) herein above and the ring can comprise one or more heteroatoms chosen from oxygen (O) sulfur (S), or nitrogen (N);

wherein each $R^{101}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or $C_3$-$C_4$ branched alkyl; the index "a" is from 0 to 4.

Stated in another way, the disclosed process relates to the formation of compounds having the formula:

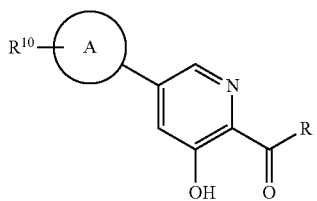

wherein the A ring represents $R^1$ units wherein $R^1$ can be:
i) substituted or unsubstituted $C_6$ or $C_{10}$ aryl; and
ii) substituted or unsubstituted $C_1$-$C_9$ heteroaryl;
wherein the substitutes for hydrogen atoms on the A ring are one or more $R^{10}$ units that are independently chosen and further described herein.

One aspect of $R^1$ relates to substituted or unsubstituted $C_6$ aryl, i.e., substituted or unsubstituted phenyl. A first embodiment of this aspect relates to $R^1$ equal to phenyl, for example, compounds having the formula:

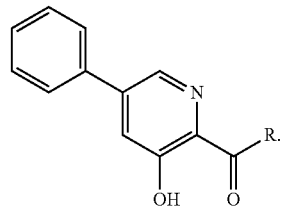

A further aspect of $R^1$ relates to $R^1$ units that are substituted phenyl having the formula:

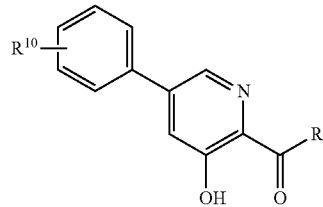

wherein $R^{10}$ represents from 1 to 5 independently chosen substitutions for hydrogen; or two $R^{10}$ units can be taken together to form a substituted or unsubstituted $C_4$-$C_8$ cycloalkyl ring, a substituted or unsubstituted $C_6$ aryl ring (phenyl), a substituted or unsubstituted $C_2$-$C_8$ heterocyclic ring, or a substituted or unsubstituted $C_3$ to $C_5$ heteroaryl ring, wherein the heterocyclic and heteroaryl rings comprise one or more hetero atoms independently chosen from oxygen (O), nitrogen (N), or sulfur (S).

One embodiment of this aspect of $R^1$ units relates to compounds comprising substitutions on $R^1$ of one or more units independently chosen from:
i) $C_1$-$C_{12}$ linear, $C_3$-$C_{12}$ branched or $C_3$-$C_{12}$ cyclic alkyl;
ii) $C_1$-$C_{12}$ linear, $C_3$-$C_{12}$ branched or $C_3$-$C_{12}$ cyclic alkoxy; and
iii) halogen: —F, —Cl, —Br, and —I.

One iteration of this embodiment relates to compounds comprising one or more $R^{10}$ units that are halogen, thereby forming the following non-limiting examples of $R^1$ units: 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 2-bromophenyl, 3-bromophenyl, 4-bromophenyl, 3,5-dichlorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

A further iteration relates to compounds comprising one or more $R^{10}$ units that are $C_1$-$C_4$ linear, $C_3$-$C_4$ branched or $C_3$-$C_4$ cyclic alkyl, thereby forming the following non-limiting examples of $R^1$ units: 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Another iteration relates to compounds comprising one or more $R^{10}$ units that are $C_1$-$C_4$ linear, $C_3$-$C_4$ branched or $C_3$-$C_4$ cyclic alkoxy, thereby forming the following non-limiting examples of $R^1$ units: 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 2-ethoxyphenyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxyphenyl, 2-isopropoxyphenyl, 3-isopropoxyphenyl, and 4-isopropoxyphenyl.

A yet still further iteration relates to compounds comprising one or more $R^{10}$ units that comprise at least one of each substitution chosen from $C_1$-$C_4$ linear or halogen, thereby forming the following non-limiting examples of R units: 2-chloro-3-methylphenyl, 2-chloro-4-methylphenyl, 2-chloro-5-methylphenyl, 2-chloro-6-methylphenyl, 3-chloro-2-methylphenyl, 3-chloro-4-methylphenyl, 3-chloro-5-methylphenyl, 3-chloro-6-methyl-phenyl, 2-fluoro-3-methylphenyl, 2-fluoro-4-methylphenyl, 2-fluoro-5-methylphenyl, 2-fluoro-6-methylphenyl, 3-fluoro-2-methylphenyl, 3-fluoro-4-methylphenyl, 3-fluoro-5-methylphenyl, and 3-fluoro-6-methylphenyl.

One embodiment of this aspect of $R^1$ units relates to compounds comprising one or more $R^{10}$ units independently chosen from:
i) —$(CR^{102a}R^{102b})_a$CN;
ii) —$(CR^{102a}R^{102b})_a$NO$_2$; and
iii) —$(CH_jX_k)_a$CH$_{j'}$X$_{k'}$; wherein X is halogen, the index j is an integer from 0 to 2, j+k=3; the index j' is an integer from 0 to 2, j'+k'=2.

On iteration of this embodiment relates to compounds comprising one or more $R^{10}$ units that are —$(CH_2)_a$CN, wherein the index a is 0 or 1, thereby forming the following non-limiting examples of $R^1$ units: 2-cyanophenyl, 3-cyanophenyl, 4-cyanophenyl, 2-(cyanomethyl)phenyl, 3-(cyanomethyl)phenyl, 4-(cyanomethyl)phenyl, 2,3-dicyanophenyl, 3,4-dicyanophenyl, and 3,5-dicyanophenyl.

Another iteration of this embodiment relates to compounds comprising one or more $R^{10}$ units that are —$(CH_2)_a$NO$_2$, wherein the index a is 0 or 1, thereby forming the following non-limiting examples of $R^1$ units: 2-nitrophenyl, 3-nitrophenyl, 4-nitrophenyl, 2-(nitromethyl)phenyl, 3-(nitromethyl)phenyl, 4-(nitromethyl)phenyl, 2,3-dinitrophenyl, 3,4-dinitrophenyl, and 3,5-dinitrophenyl.

A further iteration of this embodiment relates to compounds comprising one or more $R^{10}$ units that are —$CH_jX_k$; wherein X is halogen, the index j is an integer from 0 to 2, j+k=3, wherein the index a is 0 or 1, thereby forming the following non-limiting examples of $R^1$ units: —CH$_2$F, —CH$_2$CH$_2$F, —CHF$_2$, —CH$_2$CHF$_2$, —CF$_3$, —CH$_2$CF$_3$, —CHFCH$_2$F, —CF$_2$CHF$_2$, —CF$_2$CF$_3$, —CH$_2$Cl, —CH$_2$CH$_2$C$_1$, —CHCl$_2$, —CH$_2$CHCl$_2$, —CCl$_3$, —CH$_2$CCl$_3$, —CHClCH$_2$Cl, —CCl$_2$CHCl$_2$, and —CCl$_2$CCl$_3$.

One embodiment of this aspect of $R^1$ units relates to compounds comprising one or more $R^{10}$ units independently chosen from:
i) —$(CR^{102a}R^{102b})_a$N($R^{101}$)$_2$;
ii) —$(CR^{102a}R^{102b})_a$C(O)N($R^{101}$)$_2$; and
iii) —$(CR^{102a}R^{102b})_a$N($R^{101}$)C(O)$_2$$R^{101}$.

One iteration of this embodiment relates to compounds comprising one or more $R^{10}$ units that are —$(CR^{102a}R^{102b})_a$N($R^{101}$)$_2$, wherein the index a is 0 or 1, thereby forming the following non-limiting examples of $R^1$ units: 2-aminophenyl, 3-aminophenyl, 4-aminophenyl, 2,3-diaminophenyl, 3,4-diaminophenyl, 3,5-diaminophenyl, 2-methylaminophenyl, 3-methylaminophenyl, 4-methylaminophenyl, 2,3-(dimethylamino)phenyl, 3,4-(dimethylamino)phenyl, 3,5-(dimethylamino)phenyl, 2,3,4-triaminophenyl, 2,3,5-triaminophenyl, 2,3,6-triaminophenyl, 2,4,5-triaminophenyl, 2,4,6-triaminophenyl, 2,4-(dimethylamino)phenyl, 2,5-(dimethylamino)phenyl, 2,6-(dimethylamino)phenyl, 3,4-(dimethylamino)phenyl, 2,3,4-(dimethylamino)phenyl, 2,3,5-(dimethylamino)phenyl, 2,3,6-(dimethylamino)phenyl, 2,4,5-(dimethylamino)phenyl, 3,4,5-(dimethylamino)phenyl, and 2,4,6-(dimethylamino)phenyl.

Another iteration of this embodiment relates to compounds comprising one or more $R^{10}$ units that are —$(CR^{102a}R^{102b})_a$C(O)N($R^{101}$)$_2$, wherein $R^{101}$ is chosen from hydrogen, $C_1$-$C_6$ linear, $C_3$-$C_6$ branched alkyl or $C_3$-$C_6$ cyclic alkyl, and the index a is 0 or 1, thereby forming the following non-limiting examples of $R^1$ units: —C(O)NH$_2$, —C(O)NHCH$_3$, —CH$_2$C(O)NHCH$_3$, —C(O)N(CH$_3$)$_2$, —CH$_2$C(O)N(CH$_3$)$_2$, —C(O)NHCH$_2$CH$_3$, —CH$_2$C(O)NHCH$_2$CH$_3$, —C(O)N(CH$_2$CH$_3$)$_2$, —CH$_2$C(O)N(CH$_2$CH$_3$)$_2$, —C(O)NHCH(CH$_3$)$_2$, —CH$_2$C(O)NHCH(CH$_3$)$_2$, —C(O)N[CH(CH$_3$)$_2$]$_2$, and —CH$_2$C(O)N[CH(CH$_3$)$_2$]$_2$.

Another iteration of this embodiment relates to compounds comprising one or more $R^{10}$ units that are —$(CR^{102a}R^{102b})_a$C(O)N($R^{101}$)$_2$, wherein two $R^{101}$ units are taken together to form a ring having from 3 to 7 atoms and the index a is 0 or 1, thereby forming $R^1$ units having, for example, the formulae:

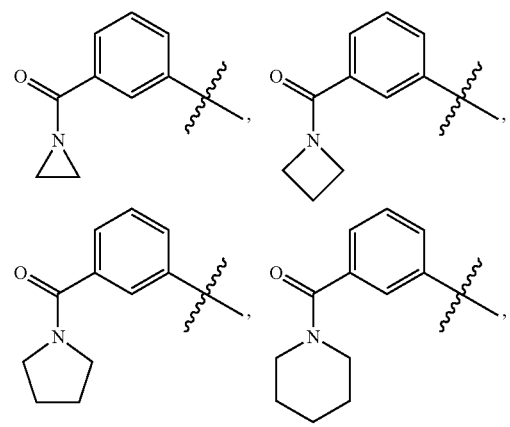

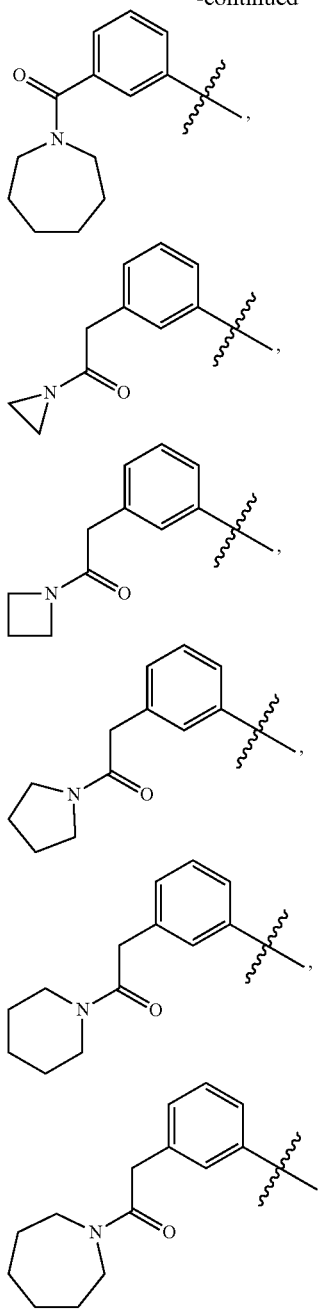

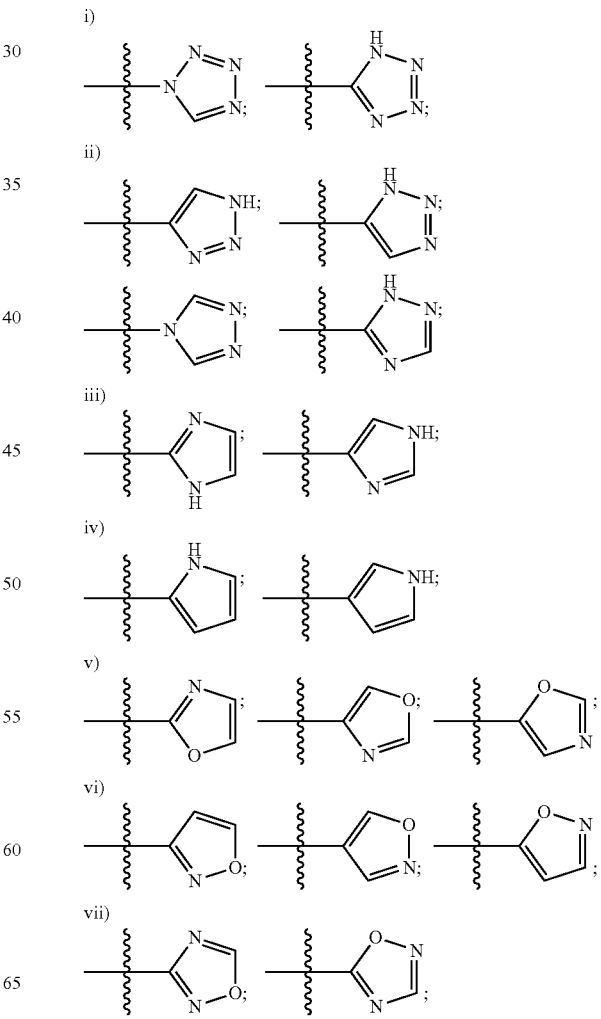

wherein ring A represent a $C_1$-$C_9$ heteroaryl unit non-limiting examples of which include: 1,2,3,4-tetrazolyl ($C_1$), [1,2,3]triazolyl ($C_2$), [1,2,4]triazolyl ($C_2$), [1,2,4]oxadiazolyl ($C_2$), [1,3,4]oxadiazolyl ($C_2$), [1,2,4]thiadiazolyl ($C_2$), [1,3,4]thiadiazolyl ($C_2$), isothiazolyl ($C_3$), thiazolyl ($C_3$), imidazolyl ($C_3$), oxazolyl ($C_3$), isoxazolyl ($C_3$), pyrazolyl ($C_3$), pyrrolyl ($C_4$), furanyl ($C_4$), thiophenyl ($C_4$), triazinyl ($C_3$), pyrimidinyl ($C_4$), pyrazinyl ($C_4$), pyridazinyl ($C_4$), pyridinyl ($C_5$), purinyl ($C_5$), xanthinyl ($C_5$), hypoxanthinyl ($C_5$), benzimidazolyl ($C_7$), indolyl ($C_8$), quinazolinyl ($C_8$), quinolinyl ($C_9$), and isoquinolinyl ($C_9$).

In a further embodiment of this aspect the $C_1$-$C_9$ heteroaryl unit can be bonded to the core pyridine ring at any suitable position, non-limiting examples of which include:

A further iteration of this embodiment relates to compounds comprising one or more $R^{10}$ units that are —$(CR^{102a}R^{102b})_aN(R^{101})C(O)_2R^{101}$; wherein $R^{101}$ is chosen from hydrogen, $C_1$-$C_6$ linear, $C_3$-$C_6$ branched alkyl or $C_3$-$C_6$ cyclic alkyl, and the index a is 0 or 1, thereby forming the following non-limiting examples of $R^1$ units: —NHC(O)CH$_3$, —CH$_2$NHC(O)CH$_3$, —NHC(O)CH$_2$CH$_3$, —CH$_2$NHC(O)CH$_2$CH$_3$, —NHC(O)CH$_2$CH$_2$CH$_3$, —CH$_2$NHC(O)CH$_2$CH$_2$CH$_3$, —NHC(O)(cyclopropyl), and —CH$_2$NHC(O)(cyclopropyl).

Another aspect of $R^1$ relates to $R^1$ units that are substituted or unsubstituted $C_1$-$C_9$ heteroaryl. One embodiment of this aspect relates to $R^1$ equal to $C_1$-$C_9$ heteroaryl, for example, compounds having the formula:

-continued
viii)
ix)
x)
xi)
xii)
xiii)
xiv)
xv)
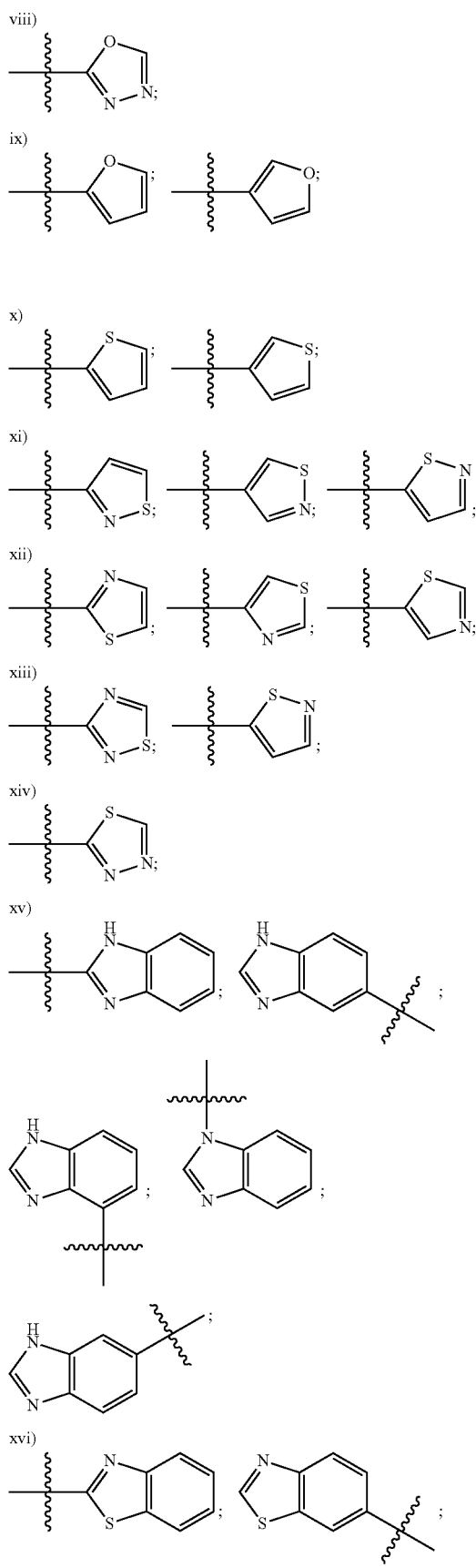
xvi)
-continued
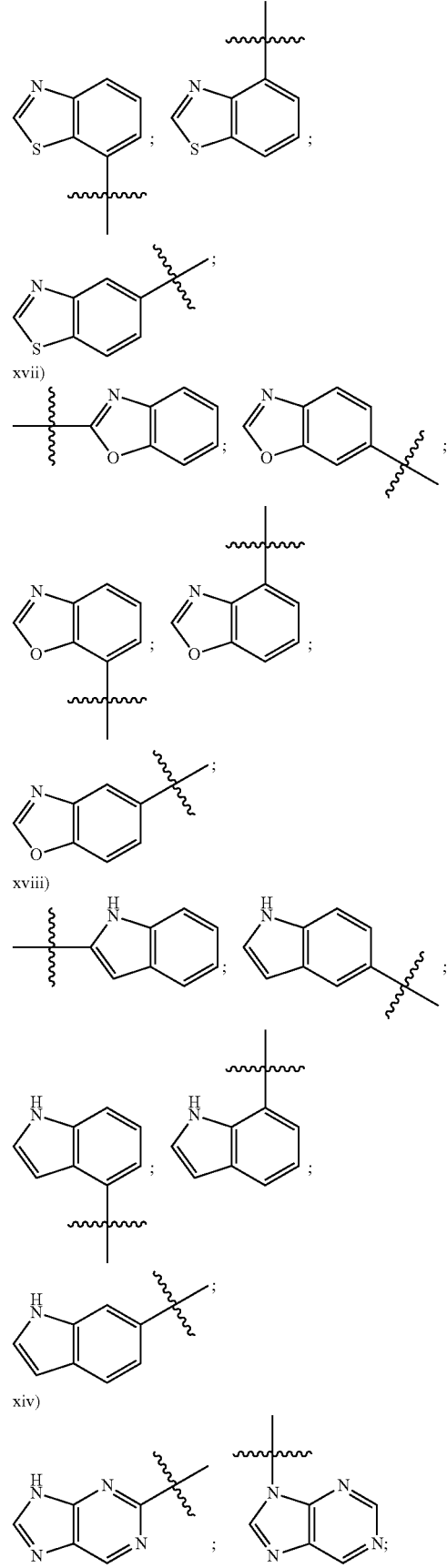
xvii)
xviii)
xiv)

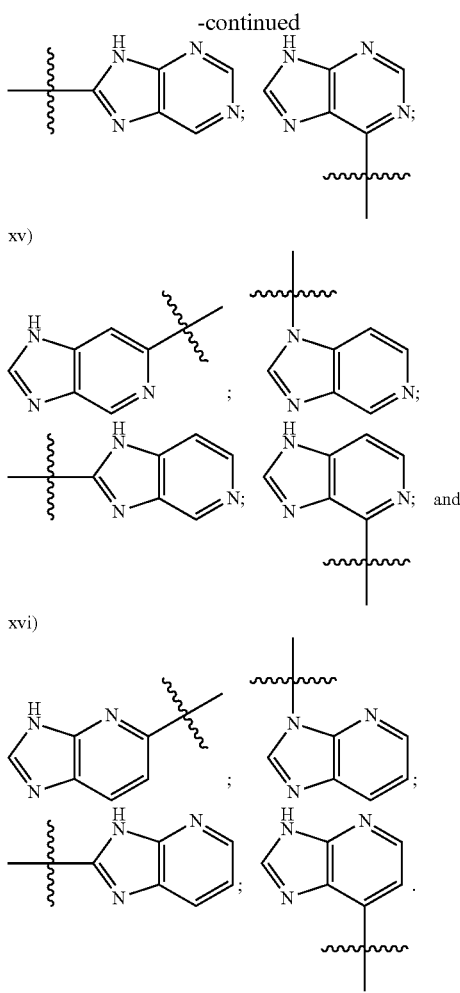

xv)

xvi)

Another embodiment of this aspect relates to $R^1$ units equal to substituted $C_1$-$C_9$ heteroaryl, for example, compounds having the formula:

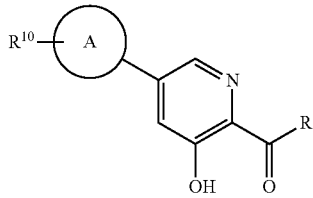

wherein ring A represent a $C_1$-$C_9$ heteroaryl unit non-limiting examples of which include: 1,2,3,4-tetrazolyl ($C_1$), [1,2,3]triazolyl ($C_2$), [1,2,4]triazolyl ($C_2$), [1,2,4]oxadiazolyl ($C_2$), [1,3,4]oxadiazolyl ($C_2$), [1,2,4]thiadiazolyl ($C_2$), [1,3,4]thiadiazolyl ($C_2$), isothiazolyl ($C_3$), thiazolyl ($C_3$), imidazolyl ($C_3$), oxazolyl ($C_3$), isoxazolyl ($C_3$), pyrazolyl ($C_3$), pyrrolyl ($C_4$), furanyl ($C_4$), thiophenyl ($C_4$), triazinyl ($C_3$), pyrimidinyl ($C_4$), pyrazinyl ($C_4$), pyridazinyl ($C_4$), pyridinyl ($C_5$), purinyl ($C_5$), xanthinyl ($C_5$), hypoxanthinyl ($C_5$), benzimidazolyl ($C_7$), indolyl ($C_8$), quinazolinyl ($C_8$), quinolinyl ($C_9$), and isoquinolinyl ($C_9$).

Non-limiting examples of substitutions for a hydrogen atom on $R^1$ $C_1$-$C_9$ heteroaryl units include:
i) $C_1$-$C_{12}$ linear, $C_3$-$C_{12}$ branched, or $C_3$-$C_{12}$ cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) $C_6$ or $C_{10}$ aryl; for example, phenyl, naphthyl (also referred to herein as naphthylen-1-yl ($C_{10}$) or naphthylen-2-yl ($C_{10}$));
iii) $C_7$ or $C_{11}$ alkylenearyl; for example, benzyl, 2-phenylethyl, naphthylen-2-ylmethyl;
iv) $C_1$-$C_9$ heterocyclic rings; as described herein below;
v) $C_1$-$C_9$ heteroaryl rings; as described herein below;
vi) $-(CR^{102a}R^{102b})_aOR^{101}$; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;
vii) $-(CR^{102a}R^{102b})_aC(O)R^{101}$; for example, $-COCH_3$, $-CH_2COCH_3$, $-COCH_2CH_3$, $-CH_2COCH_2CH_3$, $-COCH_2CH_2CH_3$, and $-CH_2COCH_2CH_2CH_3$;
viii) $-(CR^{102a}R^{102b})_aC(O)OR^{101}$; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;
ix) $-(CR^{102a}R^{102b})_aC(O)N(R^{101})_2$; for example, $-CONH_2$, $-CH_2CONH_2$, $-CONHCH_3$, $-CH_2CONHCH_3$, $-CON(CH_3)_2$, and $-CH_2CON(CH_3)_2$;
x) $-(CR^{102a}R^{102b})_aN(R^{101})C(O)R^{101}$; for example, $-NHCOCH_3$, $-CH_2NHCOCH_3$, $-NHCOCH_2CH_3$, and $-CH_2NHCOCH_2CH_3$;
xi) $-(CR^{102a}R^{102b})_aN(R^{101})C(O)_2R^{101}$; for example, $-NHCO_2CH_3$, $-CH_2NHCO_2CH_3$, $-NHCO_2CH_2CH_3$, and $-CH_2NHCO_2CH_2CH_3$;
xii) $-(CR^{102a}R^{102b})_aN(R^{101})_2$; for example, $-NH_2$, $-CH_2NH_2$, $-NHCH_3$, $-CH_2NHCH_3$, $-N(CH_3)_2$, and $-CH_2N(CH_3)_2$;
xiii) halogen; $-F$, $-Cl$, $-Br$, and $-I$;
xiv) $-(CR^{102a}R^{102b})_aCN$;
xv) $-(CR^{102a}R^{102b})_aNO_2$;
xvi) $-(CH_jX_k)_aCH_{j'}X_{k'}$; wherein X is halogen, the index j is an integer from 0 to 2, j+k=3; the index j' is an integer from 0 to 2, j'+k'=2; for example, $-CH_2F$, $-CHF_2$, $-CF_3$, $-CCl_3$, or $-CBr_3$;
xvii) $-(CR^{102a}R^{102b})_aSR^{101}$; $-SH$, $-CH_2SH$, $-SCH_3$, $-CH_2SCH_3$, $-SC_6H_5$, and $-CH_2SC_6H_5$;
xviii) $-(CR^{102a}R^{102b})_aSO_2R^{101}$; for example, $-SO_2H$, $-CH_2SO_2H$, $-SO_2CH_3$, $-CH_2SO_2CH_3$, $-SO_2C_6H_5$, and $-CH_2SO_2C_6H_5$; and
xix) $-(CR^{102a}R^{102b})_aSO_3R^{101}$; for example, $-SO_3H$, $-CH_2SO_3H$, $-SO_3CH_3$, $-CH_2SO_3CH_3$, $-SO_3C_6H_5$, and $-CH_2SO_3C_6H_5$;
wherein each $R^{101}$ is independently hydrogen, substituted or unsubstituted $C_1$-$C_6$ linear, $C_3$-$C_6$ branched, or $C_3$-$C_6$ cyclic alkyl, phenyl, benzyl, heterocyclic, or heteroaryl; or two $R^{101}$ units can be taken together to form a ring comprising 3-7 atoms; $R^{102a}$ and $R^{102b}$ are each independently hydrogen or $C_1$-$C_4$ linear or $C_3$-$C_4$ branched alkyl; the index "a" is from 0 to 4.

Non-limiting examples of substituted $C_5$-$C_9$ $R^1$ heteroaryl units include 2-methylthiazol-4-yl, 2-ethylthiazol-4-yl, 2-(n-propyl)thiazol-4-yl, 2-(iso-propyl)thiazol-4-yl, 4,5-dimethylthiazol-2-yl, 4-ethyl-5-methylthiazol-2-yl, 4-methyl-5-ethylthiazol-2-yl, 4,5-diethylthiazol-2-yl, 3-methyl-1,2,4-oxadiazol-5-yl, 4,5-dimethylimidazol-2-yl, 4-ethyl-5-methylimidazol-2-yl, 4-methyl-5-ethylimidazol-2-yl, 4,5- diethylimidazol-2-yl, 2,5-dimethylthiazol-4-yl, 2,4-dimethylthiazol-5-yl, 3-methyl-1,2,4-oxadiazol-5-yl, 4,5-dimethyloxazol-2-yl, 4-ethyl-5-methyloxazol-2-yl, 4-methyl-5-ethyloxazol-2-yl, 4,5-diethyloxazol-2-yl, 2-methyloxazol-4-yl, 2-ethyloxazol-4-yl, 2-(n-propyl)oxazol-4-yl, 2-(iso-propyl)oxazol-4-yl, 2-methyloxazol-4-yl, 2-ethyloxazol-4-yl, 2-(n-propyl)oxazol-4-yl, 2-(iso-propyl)oxazol-4-yl, 5-methyl[1,2,4]oxadiazol-3-yl, 5-ethyl[1,2,4]-oxadiazol-3-yl, 5-propyl[1,2,4]oxadiazol-3-yl, 5-cyclopropyl[1,2,4]oxadiazol-3-yl, 3-methyl[1,2,4]oxadiazol-5-yl, 3-ethyl[1,2,4]oxadiazol-5-yl, 3-(n-propyl)[1,2,4]oxadiazol-5-yl, 3-(iso-propyl)[1,2,4]oxadiazol-5-yl, 2,5-dimethylthiazol-4-yl, 2,4-dimethylthiazol-5-yl, 4-ethylthiazol-2-yl, 3-methyl-1,2,4-oxadiazol-5-yl, 4,5-dimethylpyrimidin-2-yl, 4,5-diethylpyrimidin-2-yl, 4-methyl-5-ethyl-pyrimidin-2-yl, 4-ethyl-5-methyl-pyrimidin-2-yl, 4-(thiophen-2-yl)pyrimidin-2-yl, 5-(thiophen-2-yl)pyrimidin-2-yl, 4-(thiophen-3-yl)pyrimidin-2-yl, and 5-(thiophen-2-yl)pyrimidin-3-yl.

Non-limiting examples of substituted $C_2$-$C_4$ 5-member heteroaryl rings include:

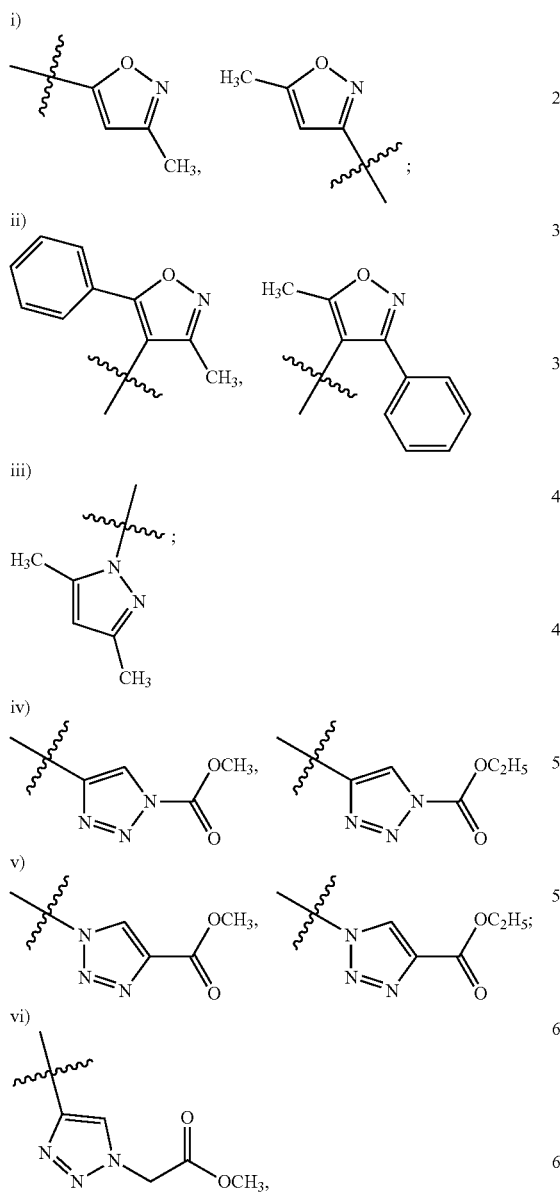

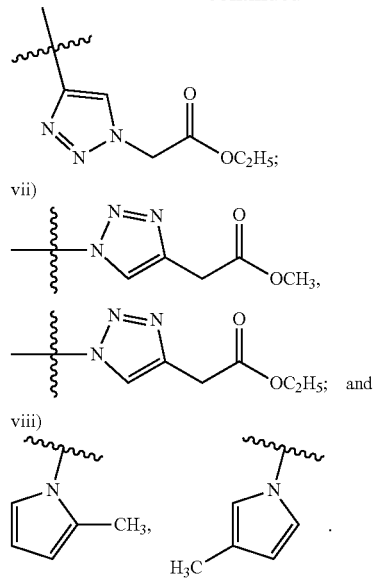

A yet further aspect of $R^1$ units relates to rings comprising two $R^{10}$ substitutions for hydrogen that are taken together to form a substituted or unsubstituted $C_2$-$C_8$ heterocyclic ring. One embodiment of this aspect relates to $R^1$ units wherein two $R^{10}$ units are taken together to form a substituted or unsubstituted $C_7$-$C_9$ heterocyclic $R^1$ ring system wherein the heterocyclic ring formed by the two $R^{10}$ substitutions contains one or more nitrogen atoms. Non-limiting iterations of this embodiment include $R^1$ units having the formulae:

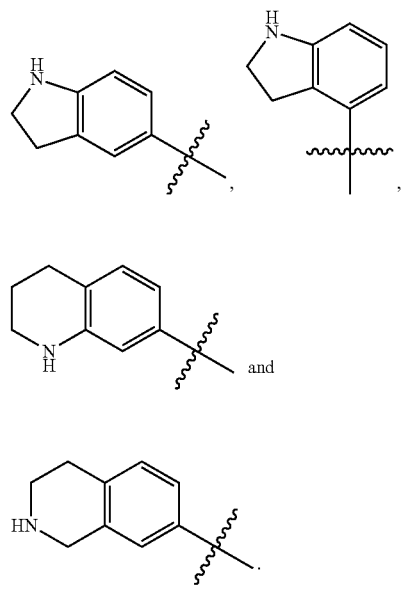

Another embodiment of this aspect relates to $R^1$ units wherein two $R^{10}$ units are taken together to form a substituted or unsubstituted $C_7$-$C_9$ heterocyclic $R^1$ ring system wherein the heterocyclic ring formed by the two $R^{10}$ substitutions contains one or more oxygen atoms. Non-limiting iterations of this embodiment include $R^1$ units having the formulae:

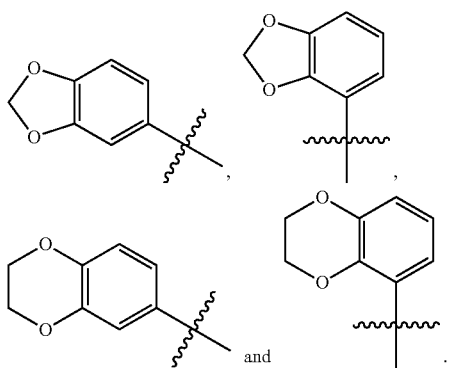

R² Units

R² units are chosen from $C_1$-$C_{12}$ linear alkyl or $C_3$-$C_{12}$ branched alkyl. In one embodiment R² can represent hydrogen. In another embodiment, R² is $C_1$-$C_4$ linear alkyl. Non-limiting examples include methyl, ethyl and n-propyl. In one example, R² is methyl.

R² units relate to the alkoxide unit having the formula:

that is used in the process disclosed herein. As it relates to the alkoxide, the alkoxide can be derived from any suitable source, i.e., sodium methoxide, lithium ethoxide, and the like which the formulator can choose.

A further aspect of the present disclosure relates to a process for preparing intermediates having the formula:

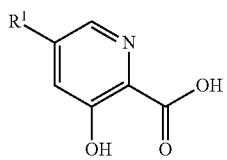

wherein R¹ is the same as defined herein above. This aspect also includes salts of acids, for example, compounds having the formula:

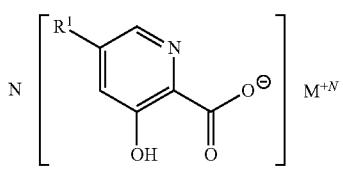

wherein M is a salt forming cation and N represents the cationic charge on M and the number of corresponding anionic units of the disclosed intermediates. The M units can comprise in one embodiment inorganic cations, inter alia, ammonium, sodium, lithium, potassium, calcium, magnesium, bismuth, and the like. In another embodiment, M units can comprise organic cation forming units, inter alia, lysine, ornithine, glycine, alanine, or other amino acids, basic organic compounds, inter alia, methylamine, dimethylamine, trimethylamine, and the like.

Another aspect of the present disclosure relates to a process for preparing intermediates having the formula:

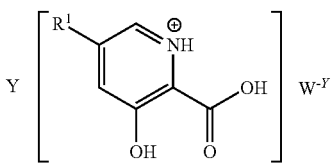

wherein W is a salt forming anion and Y represents the anionic charge on W and the number of corresponding number of the disclosed intermediates in this salt form. The W units can comprise in one embodiment inorganic anions, inter alia, chloride, bromide, iodide, sulfate, bisulfate, carbonate, bicarbonate, phosphate, and the like. In another embodiment, W units can comprise organic anion forming units, inter alia, formate, acetate, propionate, butyrate, pyruvate, lactate, oxalate, malonate, maleate, succinate, tartrate, fumarate, citrate, and the like.

In one aspect, the disclosed prolyl hydroxylase inhibitors can be isolated as a pharmaceutically acceptable salt having the formula:

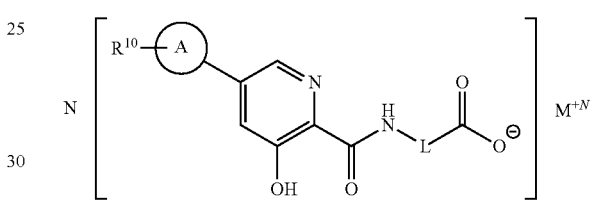

wherein M is a salt forming cation and N represents the cationic charge on M and the number of corresponding anionic units present in the salt.

One aspect of the disclosed salts relates to prolyl hydroxylase inhibitors in the form of the mono-valent salt having the formula:

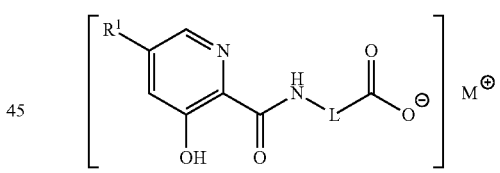

wherein M represents an inorganic or organic cation. Non-limiting examples of mono-valent cations include sodium, lithium, potassium, ammonium, silver, organic cations having the formula $HN^+R^aR^bR^c$ wherein $R^a$, $R^b$ and $R^c$ are each independently:
  i) hydrogen;
  ii) substituted or unsubstituted $C_1$-$C_{12}$ linear, $C_3$-$C_{12}$ branched, or $C_3$-$C_{12}$ cyclic alkyl;
  iii) substituted or unsubstituted benzyl;
wherein one or more of $R^a$, $R^b$ and $R^c$ can be independently substituted by one or more units chosen from:
  i) $C_1$-$C_{12}$ linear, $C_3$-$C_{12}$ branched, or $C_3$-$C_{12}$ cyclic alkoxy;
  ii) $C_1$-$C_{12}$ linear, $C_3$-$C_{12}$ branched, or $C_3$-$C_{12}$ cyclic haloalkoxy;
  iii) halogen;
  iv) hydroxyl;
  v) thio; or vi) one or more of $R^a$, $R^b$ and $R^c$ can contain one or more units capable of forming a cation, anion, or zwitterions.

One iteration of this embodiment relates to cations wherein each of $R^a$, $R^b$ and $R^c$ are hydrogen or $C_1$-$C_{12}$ linear alkyl. Non-limiting examples include methyl ammonium [HN$^+$H$_2$(CH$_3$)], dimethyl ammonium [HN$^+$H(CH$_3$)$_2$], trimethyl ammonium [HN$^+$(CH$_3$)$_3$], ethyl ammonium [HN$^+$H$_2$(CH$_2$CH$_3$)], diethyl ammonium [HN$^+$H(CH$_2$CH$_3$)$_2$], triethyl ammonium [HN(CH$_2$CH$_3$)$_3$], dimethylethyl ammonium [HN$^+$(CH$_3$)$_2$(CH$_2$CH$_3$)], and methyldiethyl ammonium [HN$^+$(CH$_3$)(CH$_2$CH$_3$)$_2$].

Another iteration of this embodiment relates to cations wherein one or more of $R^a$, $R^b$ and $R^c$ are chosen from hydrogen, unsubstituted $C_1$-$C_{12}$ linear, $C_3$-$C_{12}$ branched, or $C_3$-$C_{12}$ cyclic alkyl or substituted $C_1$-$C_{12}$ linear, $C_3$-$C_{12}$ branched, or $C_3$-$C_{12}$ cyclic alkyl. One embodiment relates to organic cations having one or more $C_1$-$C_{12}$ linear, $C_3$-$C_{12}$ branched, or $C_3$-$C_{12}$ cyclic alkyl chains substituted with hydroxy. Non-limiting examples include 2-hydroxyethyl ammonium (cation of monoethanolamine, cholinate) [HN$^+$H$_2$(CH$_2$CH$_2$OH)], methyl-2-hydroxyethyl ammonium [H$_2$N$^+$(CH$_3$)(CH$_2$CH$_2$OH)], di(2-hydroxyethyl) ammonium [H$_2$N$^+$(CH$_2$CH$_2$OH)$_2$], tri(2-hydroxyethyl) ammonium [HN$^+$(CH$_2$CH$_2$OH)$_3$], and tris(hydroxymethyl)methyl ammonium (cation of tris(hydroxymethyl)aminomethane) [H$_3$N$^+$C[(CH$_2$H)]3]. Also included are cations formed from amino sugars, for example, amino sugars having the formula H$_2$N$^+$(CH$_3$)[(CHOH)$_n$CH$_2$H] wherein n is from 1 to 7. A non-limiting example of an amino sugar suitable for forming an organic cation is meglumine (1-deoxy-1-methylaminosorbitol).

A further iteration of this embodiment relates to cations formed from amino acids. Non-limiting examples include lysine, ornithine, arginine, glutamine, and the like.

Another aspect of organic amines suitable for forming salts of the disclosed stabilizer include amines wherein one or more of $R^a$, $R^b$ and $R^c$ are taken together to form a heterocyclic ring that can comprise from 3 to 20 atoms and optionally one or more heteroatoms chosen from nitrogen, oxygen and sulfur. Non-limiting examples include piperazine, piperidine, morpholine, thiomorpholine, and the like.

In addition, di-valent cations can be used wherein the salts of these examples have the formula:

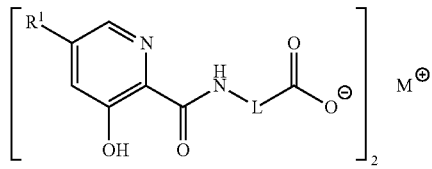

Non-limiting examples of di-valent cations includes calcium magnesium, barium and the like.

Another example of salts includes the di-anions having the formula:

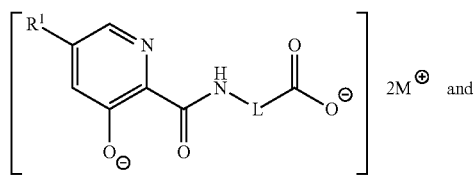

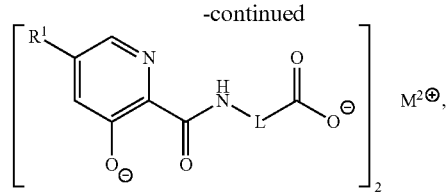

wherein M is the same as defined herein above.

The importance of the herein disclosed intermediates lies in the fact that the formulator can prepare an admixture comprising a plurality of final compounds in one step by the choice of reactants in the final process step as described herein. For example, it is known by the artisan that, although two or more analogs can have approximately equal pharmacological activity, other properties such as bioavailability can be different. Using the disclosed intermediates to form admixtures of final analogs can provide the formulator with a final composition which utilizes the disparate pharmacological activities of the molecules to provide for a constant level of a desired property. For example, one analog in the admixture can have immediate bioavailability while a second or third compound has a slower bioavailability which can provide a pharmacologically active composition that has a steady or near steady level of drug active in a user.

Process

Disclosed herein is a process for preparing the herein above disclosed [(5-phenyl-3-hydroxypyridine-2-carbonyl)-amino]alkanoic acids and [(5-heteroaryl-3-hydroxypyridine-2-carbonyl)-amino]alkanoic acids. As disclosed herein, the 5-phenyl and 5-heteroaryl rings can be substituted by one or more independently chosen substitutions for hydrogen.

The following is a summary of the steps that comprise the disclosed process.

Step A

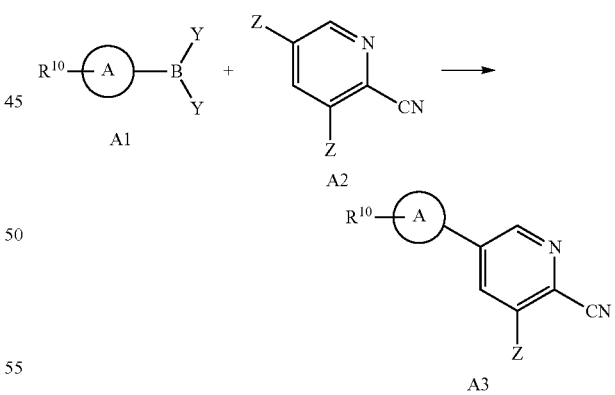

Step A relates to the condensation of an aryl or heteroaryl borate precursor, A1, and a 3,5-dihalo-2-cyanopyridine, A2, wherein each Z is independently chloro or bromo, to form a 5-aryl or 5-heteroaryl-3-halo-2-cyanopyridine, A3.

The borate precursor, A1, comprises ring A wherein ring A can be:
A) substituted or unsubstituted $C_6$ or $C_{10}$ aryl; and
ii) substituted or unsubstituted $C_1$-$C_9$ heteroaryl;
wherein the substitutes for hydrogen atoms on the A ring are one or more $R^{10}$ units that are independently chosen and further described herein. Y is OR$^{20}$, wherein R$^{20}$ is hydrogen or C$_1$-C$_6$ linear, C$_3$-C$_6$ branched, or C$_3$-C$_6$ cyclic alkyl, or two OR$^{20}$ units can be taken together to form a 5-member to 7-member C$_3$-C$_{10}$ cyclic ester, for example, a cyclic ester having the formula:

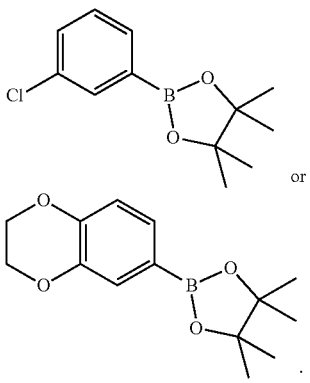

One aspect of borate precursors relates to phenyl boronic acid having the formula:

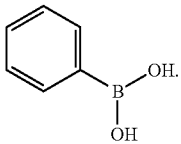

Another aspect of borate precursors relates to substituted boronic acids having the formula:

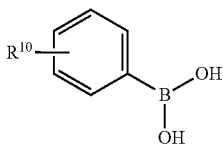

wherein R$^{10}$ represents from 1 to 5 substitutions as defined herein above. Non-limiting examples of this aspect includes borate precursors having the formula:

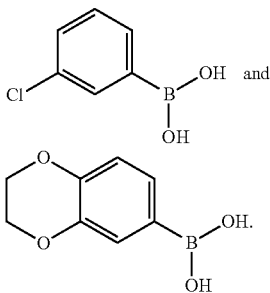

The 3,5-dihalo-2-cyanopyridine, A2, is chosen from 3,5-dichloro-2-cyanopyridine, 3-chloro-5-bromo-2-cyanopyridine, 3,5-dibromo-2-cyanopyridine and 3-bromo-5-chloro-2-cyanopyridine.

Step A is conducted in the presence of a catalyst, for example, a Suzuki coupling catalyst. The formulator can choose the catalyst and conditions that are compatible with the reagents, i.e., borate precursor and 3,5-dihalo-2-cyanopyridine. (See, Suzuki, A. Pure Appl. Chem. 1991, 63, 419-422; Suzuki, A., J. Organometallic Chem. 1999, 576, 147-168; Barder, T. E. et al., "Catalysts for Suzuki-Miyaura Coupling Processes: Scope and Studies of the Effect of Ligand Structure," J. Am. Chem. Soc. 2005, 127, 4685-4696 included herein by reference in their entirety.)

In one embodiment, the catalyst is [1,1'-bis(diphenyphosphino)ferrocene]dichloro-palladium(II) [PdCl$_2$(dppf)].

Another category of catalysts include ortho-metalated catalysts with alkylphosphine ligands of the general formula [Pd(X)(κ$^2$N,C—C$_6$H$_4$CH$_2$NMe$_2$)(PR$_3$)] wherein R is Cy, X is trifluoroacetate, trifluoromethanesufonyl, chloro, or iodo; PR$_3$ is PCy$_2$(o-biphenyl), X is trifluoroacetate). Non-limiting examples of this category include [{Pd(μ-TFA)(κ$^2$N, C—C$_6$H$_4$CH$_2$NMe$_2$)}$_2$] and [{Pd(TFA)(κ$^2$N,C—C$_6$H$_4$CH=N$^i$Pr)}$_2$].

The catalyst can be preformed, for example, purchased from a chemical supplier or the catalyst can be generated in situ. One non-limiting example of Step A wherein the catalyst is generated in situ includes the following procedure. Pd(OAc)$_2$ (1.5 mmol %), 3,3'-dimethyl-1,1'(2,4-bismethylenemesitylene)(4,4,5,6-tetrahydropyrimidinium) chloride (1.5 mmol %), a borate precursor (1.5 mmol), a 3,5-dihalo-2-cyanopyridine (1.0 mmol), K$_2$CO$_3$ (2 mmol), water (3 mL)-DMF (3 mL) are added to a small Schlenk tube and the mixture heated at 80° C. for 5 hours. At the conclusion of the reaction, the mixture is collected, removed by extraction with suitable solvent, and the desired product isolated by methods known to the artisan.

Step A is conducted in the presence of a base. Non-limiting examples of suitable bases that can be used in Step A includes LiOH, NaOH, KOH, Ca(OH)$_2$, Li$_2$CO$_3$, Na$_2$CO$_3$, K$_2$CO$_3$, and CaCO$_3$. In one embodiment, the base is K$_2$CO$_3$. In another embodiment, the base is Na$_2$CO$_3$.

Step A can be optionally conducted in the presence of a solvent. Non-limiting examples of solvents include water, formic acid, acetic acid; alcohols, for example, methanol, ethanol, 2,2,2-trichlorethanol, propanol, isopropanol, butanol, tert-butanol, and the like; ketones, for example, acetone, methyl ethyl ketone, diethyl ketone, and the like; esters, for example, methyl acetate, ethyl acetate, methyl propionate, ethyl propionate, and the like; ethers, for example, diethyl ether, methyl tert-butyl ether, tetrahydrofuran, dimethoxyethane, bis(2-methoxyethyl) ether (diglyme), 1,4-dioxane, and the like; alkanes, for example, pentane, isopentane, petroleum ether, hexane, mixtures of hexanes, cyclohexane, heptanes, isoheptane, octane, isooctane, and the like; halogenated solvents, for example, dichloromethane, chloroform, carbon tetrachloride, 1,1-dichloroethane, 1,1,1-trichloroethane, 1,2-dichloroethane, chlorobenzene, and the like; aromatic hydrocarbons, for example, benzene, toluene, 1,2-dimethylbenzene (ortho-xylene), 1,3-dimethylbenzene (meta-xylene), 1,4-dimethylbenzene (para-xylene), nitrobenzene, and the like; dipolar aprotic solvents, for example, acetonitrile, dimethylsulfoxide, N,N-dimethylformamide, N,N-diethylformamide, N,N-dimethylacetamide, N,N-diethylacetamide, N-methyl-2-pyrrolidinone, carbon disulfide, and hexamethylphosphoramide; and mixtures of one or more solvents.

The reaction can be conducted at any temperature sufficient to provide the desired products or desired products.

Step B

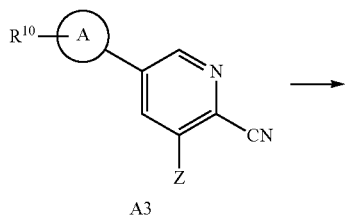

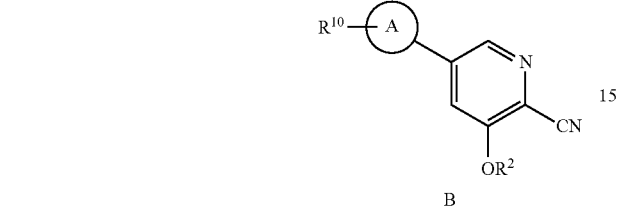

Step B relates to the conversion of a 5-aryl or 5-heteroaryl-3-halo-2-cyanopyridine, A3, to a 5-aryl or 5-heteroaryl-3-alkoxy-2-cyanopyridine, B.

Compound A3 is reacted with an alkoxide having the formula:

$$^{\ominus}OR^2$$

wherein $R^2$ is $C_1$-$C_{12}$ linear alkyl or $C_3$-$C_{12}$ branched alkyl. In one embodiment of step B, intermediate A3 can be reacted with methoxide anion. The methoxide anion can be generated in situ, for example, by the addition of an alkali metal to methanol. In one example, from 1 equivalent to 10 equivalents of sodium metal based upon the amount of A3 to be converted in Step B, is added to an excess of methanol. In another example, an alkali metal is added to an excess of methanol, the solvent removed, and the resulting sodium methoxide retained for use when, for example, Step B is conducted in a solvent other than methanol.

In another embodiment, the intermediate A3 can be reacted with ethoxide anion generated from ethanol. In still another embodiment, the intermediate A3 can be reacted with isopropoxy anion generated from isopropanol.

As such, step B can be conducted at any temperature sufficient to provide the desired products or desired products. In addition, step B can be conducted in any solvent or mixtures of solvents that do not react with methoxide anion under the conditions chosen by the formulator.

Step C

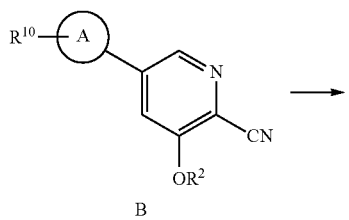

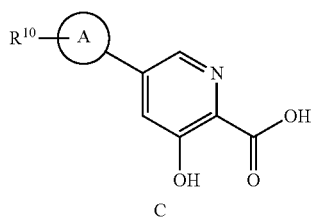

Step C relates to the conversion of the 5-aryl or 5-heteroaryl-3-alkoxy-2-cyanopyridine formed in step B to form a 5-aryl or 5-heteroaryl-3-hydroxy-2-carboxypyridine, C, (5-aryl or 5-heteroaryl-3-hydroxypicolinic acid). This conversion can be conducted in the presence of any acid capable of hydrolysis of the cyano moiety to a carboxylic acid moiety and the methoxy moiety to a hydroxyl moiety. In one embodiment, 48% aqueous HBr can be used. In another embodiment, 37% aqueous HCl can be used.

The compounds having formula C can be isolated as the free acid or as a salt, for example, as a compound having the formula:

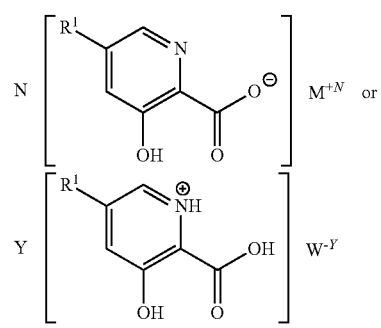

as further described herein. Depending upon the intended use of the products of step C, the formulator can proceed to step D or retain the products of step C for use in preparing admixtures of prolyl hydroxylase inhibitors or for preparing prodrugs of prolyl hydroxylase inhibitors.

Step D

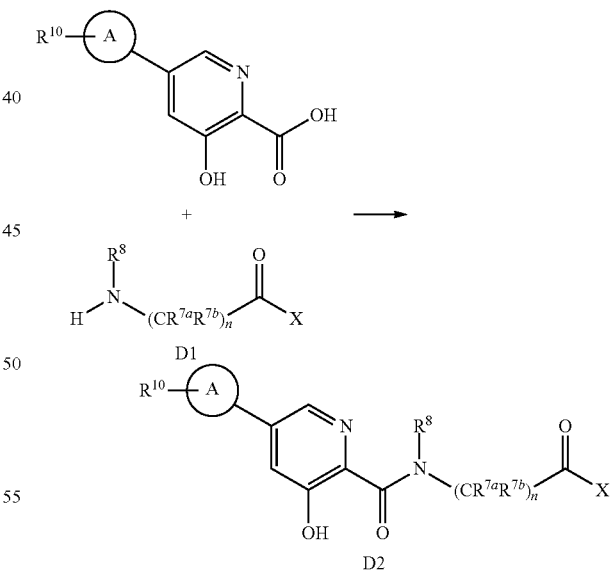

Step D relates to the reaction of the 5-aryl or 5-heteroaryl-3-hydroxy-2-carboxypyridine formed in step C with a compound having formula D1, wherein X is chosen from —OH, —$OR^3$, —$NR^4R^5$ or —$OM^1$ as defined herein above, to form one of the following:
i) a prolyl hydroxylase inhibitor;
ii) a prolyl hydroxylase inhibitor prodrug;
iii) an admixture of prolyl hydroxylase inhibitors;

iv) an admixture of prolyl hydroxylase inhibitor prodrugs; or v) suitable pharmaceutical salts thereof.

One aspect of step D relates to formation of a prolyl hydroxylase inhibitor according to the following scheme:

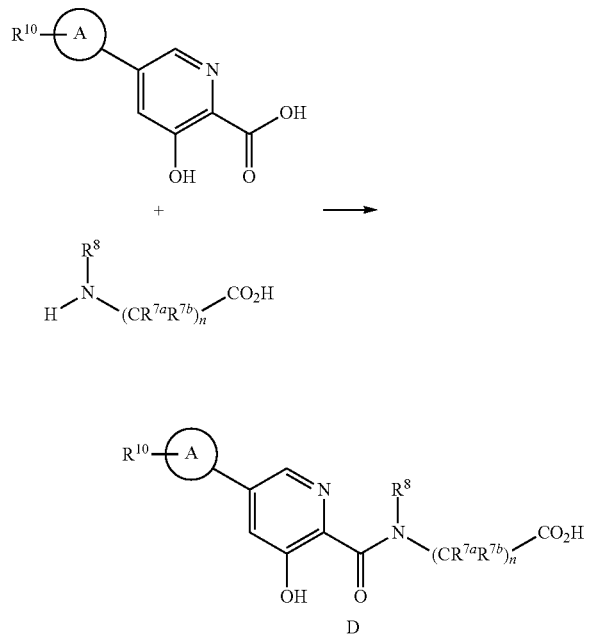

wherein $R^{7a}$, $R^{7b}$, $R^8$ and the index n are defined herein above.

Another aspect of step D relate to formation of a prolyl hydroxylase ester prodrug according to the following scheme:

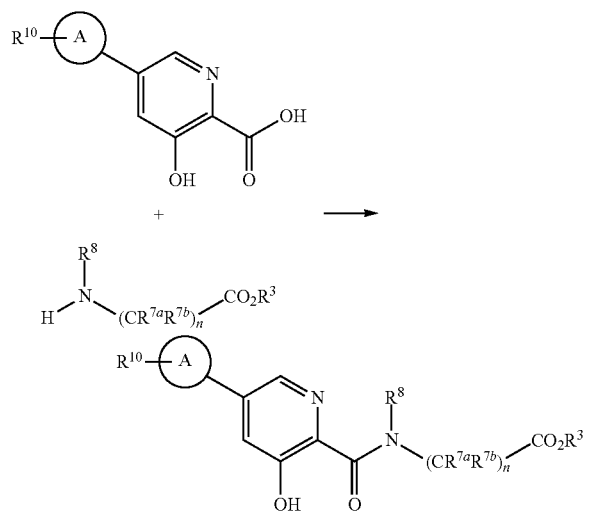

wherein $R^3$, $R^{7a}$, $R^{7b}$, $R^8$ and the index n are defined herein above.

A further aspect of step D relate to formation of a prolyl hydroxylase amide prodrug according to the following scheme:

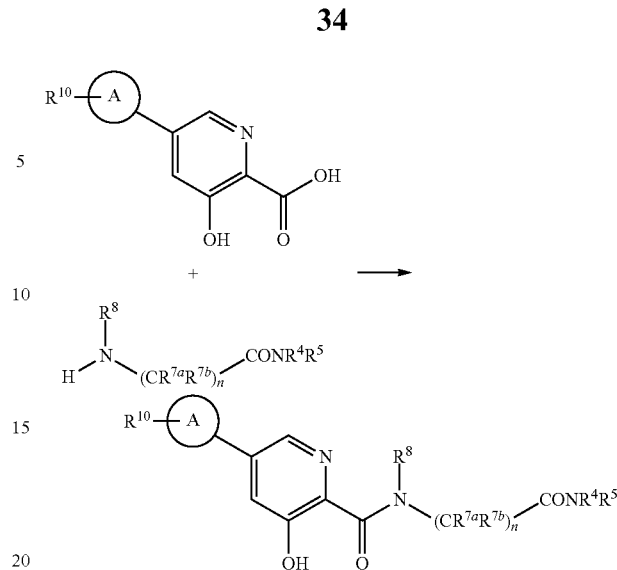

wherein $R^4$, $R^5$, $R^{7a}$, $R^{7b}$, $R^8$ and the index n are defined herein above.

Step D relates to the coupling of a 5-aryl or 5-heteroaryl-3-hydroxy-2-carboxy-pyridine, C, prepared in Step C with an amino acid, amino acid ester, or amino acid amide. Any coupling reagent compatible with the 5-aryl or 5-heteroaryl-3-hydroxy-2-carboxy-pyridine, amino acid, amino acid ester, or amino acid amide can be used to prepare the desired prolyl hydroxylase inhibitors or prodrugs thereof. Non-limiting examples of coupling reagents includes carbonyl-diimidazole (CDI), dicyclohexylcarbodiimide (DCC), diisopropylcarbodiimide (DIC), and ethyl-(N',N'-dimethylamino)propylcarbodiimide (EDC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), O-(benzotriazol-1-yl)-N,N,N'N'-tertaetyluronium hexafluorophosphate (HBTU), O-(benzotriazol-1-yl)-N,N,N'N'-tertamethyluronium tetrafluoroborate (TBTU), O-(7-azabenzotriazol-1-yl)-N,N,N'N'-tetramethyluronium hexafluorophosphate (HATU), O-(6-chlorobenzotriazol-1-yl)-N,N,N'N'-tetramethyluronium hexafluorophosphate (HCTU), O-(3,4-dihydro-4-oxo-1,2,3-benzotriazine-3-yl)-N,N,N'N'-tetramethyluronium hexafluorophosphate (TDBTU), and 3-(diethylphosphoryloxy)-1,2,3-benzotriazin-4(3H)-one (DEPBT). In one iteration, wherein $R^8$ is not hydrogen, step D can be conducted with a suitable reagent such as bromo-tris-pyrrolidino-phosphonium hexafluorophosphate (PyBrOP).

A further iteration of the reaction outlined in step D utilizes an in situ generated mixed anhydride of the 5-aryl or 5-heteroaryl-3-hydroxy-2-carboxypyridine, for example, reacting compound C with a mixed anhydride forming reagent. Non-limiting examples include isobutylchloro-formate (IBCF), ethylchoroformate, isopropylchloroformate, and the like. Other coupling reagents include 2-chloro-3,6-dimethoxy-1,3,5-triazine, pivalolyl chloride and triphosgene. In another iteration, acyl chlorides can be used to activate the carbonyl moiety of compound C for the coupling exemplified in step D.

In a yet further embodiment pivaloyl chloride in THF are used to catalyze the coupling reaction.

An organic or inorganic base can be used for conducting step D. Non-limiting examples of suitable organic bases include diisopropylethylamine, and the like.

Step D can be conducted in one or more solvents. Non-limiting examples of solvents include dimethylformamide (DMF), diethylformamide (DEF), dimethylacetamide (DMA), diethylacetamide (DEA), dimethyl sulfoxide (DMSO), dioxane, and water. In one embodiment, a mixture of water and one or more polar organic solvents can be used, for example, DMF/water, DMSO/water, dioxane/water, DMF/dioxane/water, and the like.

In some embodiments of the disclosed process, due to the type of substitution $R^{10}$ on ring A, the formulator can form a prodrug prior then further process the prodrug to the final prolyl hydroxylase inhibitor. For example, the intermediate C may comprise an $R^{10}$ unit that has a protecting group present, i.e., carbobenzyloxy, tert-butoxycarbonyl, and the like. In such examples it can be more convenient for the formulator to form the final product in prodrug form, remove the protecting group then in a Step E, hydrolyze the prodrug to the free acid. The hydrolysis can be conducted in any suitable acid or base.

The conditions of Step D can be modified by the formulator to meet the properties of the reagents.

Scheme I herein below outlines and Example 1 describes a non-limiting example of the disclosed process for the preparation of a prolyl hydroxylase ester pro-drug.

Reagents and conditions:
(a) $K_2CO_3$, $PdCl_2$(dppf), DMF; 45° C., 18 hr.

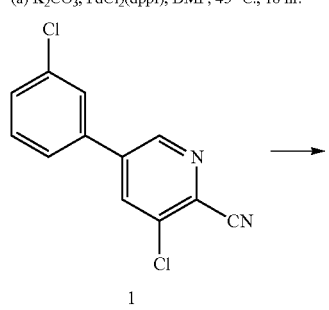

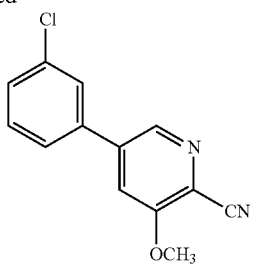

Reagents and conditions:
(b) $NaOCH_3$, $CH_3OH$; reflux, 20 hr.

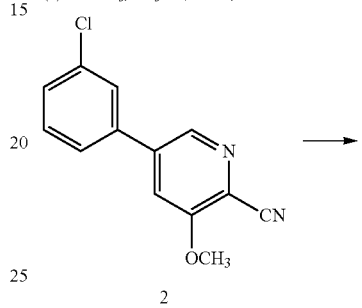

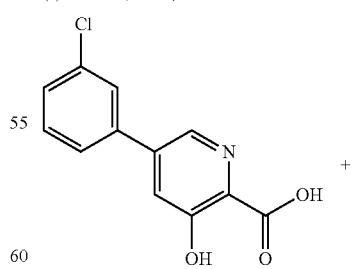

Reagents and conditions:
(c) 48% HBr; reflux, 20 hr.

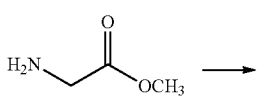

-continued

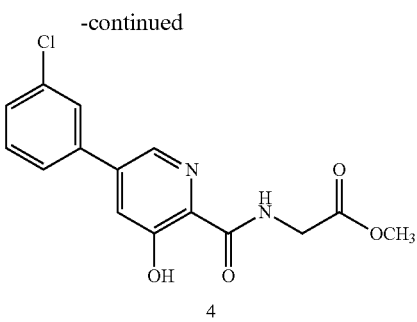

Reagents and conditions:
(d) CDI, DIPEA, DMSO; rt, 2.5 hr.

Example 1

Methyl {[5-(3-chlorophenyl)-3-hydroxypyridin-2-yl]amino}acetate (4)

Preparation of 5-(3-chlorophenyl)-3-chloro-2-cyanopyridine (1): To a 100 mL round bottom flask adapted for magnetic stirring and equipped with a nitrogen inlet was charged (3-chlorophenyl)boronic acid (5 g, 32 mmol), 3,5-dichloro-2-cyanopyridine (5.8 g, 34 mmol), $K_2CO_3$ (5.5 g, 40 mmol), [1,1'-bis(diphenyphosphino)ferrocene]dichloro-palladium(II) [$PdCl_2$(dppf)] (0.1 g, 0.13 mmol), dimethylformamide (50 mL) and water (5 mL). The reaction solution was agitated and heated to 45° C. and held at that temperature for 18 hours after which the reaction was determined to be complete due to the disappearance of 3,5-dichloro-2-cyanopyridine as measured by TLC analysis using ethyl acetate/methanol (4:1) as the mobile phase and UV 435 nm to visualize the reaction components. The reaction solution was then cooled to room temperature and the contents partitioned between ethyl acetate (250 mL) and saturated aqueous NaCl (100 mL). The organic phase was isolated and washed a second time with saturated aqueous NaCl (100 mL). The organic phase was dried for 4 hours over $MgSO_4$, the $MgSO_4$ removed by filtration and the solvent removed under reduced pressure. The residue that remained was then slurried in methanol (50 mL) at room temperature for 20 hours. The resulting solid was collected by filtration and washed with cold methanol (50 mL) then hexanes (60 mL) and dried to afford 5.8 g (73% yield) of an admixture containing a 96:4 ratio of the desired regioisomer. $^1$H NMR (DMSO-$d_6$) δ 9.12 (d, 1H), 8.70 (d, 1H), 8.03 (t, 1H) 7.88 (m, 1H), and 7.58 (m, 2H).

Preparation of 5-(3-chlorophenyl)-3-methoxy-2-cyanopyridine (2): To a 500 mL round bottom flask adapted for magnetic stirring and fitted with a reflux condenser and nitrogen inlet was charged with 5-(3-chlorophenyl)-3-chloro-2-cyanopyridine, 1, (10 g, 40 mmol), sodium methoxide (13.8 mL, 60 mmol) and methanol (200 mL). With stirring, the reaction solution was heated to reflux for 20 hours. The reaction was determined to be complete due to the disappearance of 5-(3-chlorophenyl)-3-chloro-2-cyanopyridine as measured by TLC analysis using hexane/ethyl acetate (6:3) as the mobile phase and UV 435 nm to visualize the reaction components. The reaction mixture was cooled to room temperature and combined with water (500 mL). A solid began to form. The mixture was cooled to 0° C. to 5° C. and stirred for 3 hours. The resulting solid was collected by filtration and washed with water, then hexane. The resulting cake was dried in vacuo at 40° C. to afford 9.4 g (96% yield) of the desired product as an off-white solid. $^1$H NMR (DMSO-$d_6$) δ 8.68 (d, 1H), 8.05 (d, 1H), 8.01 (s, 1H) 7.86 (m, 1H), 7.59 (s, 1H), 7.57 (s, 1H) and 4.09 (s, 3H).

Preparation of 5-(3-chlorophenyl)-3-hydroxypyridine-2-carboxylic acid (3): To a 50 mL round bottom flask adapted for magnetic stirring and fitted with a reflux condenser was charged 5-(3-chlorophenyl)-3-methoxy-2-cyanopyridine, 2, (1 g, 4 mmol) and a 48% aqueous solution of HBr (10 mL). While being stirred, the reaction solution was heated to reflux for 20 hours. The reaction was determined to be complete due to the disappearance of 5-(3-chlorophenyl)-3-methoxy-2-cyanopyridine as measured by TLC analysis using hexane/ethyl acetate (6:3) as the mobile phase and UV 435 nm to visualize the reaction components. The reaction contents was then cooled to 0° C. to 5° C. with stirring and the pH was adjusted to approximately 2 by the slow addition of 50% aqueous NaOH. Stirring was then continued at 0° C. to 5° C. for 3 hours. The resulting solid was collected by filtration and washed with water, then hexane. The resulting cake was dried in vacuo at 40° C. to afford 1.03 g (quantitative yield) of the desired product as an off-white solid. $^1$H NMR (DMSO-$d_6$) δ 8.52 (d, 1H), 7.99 (d, 1H), 7.95 (s, 1H) 7.81 (t, 1H), 7.57 (s, 1H), and 7.55 (s, 1H).

Preparation of methyl {[5-(3-chlorophenyl)-3-hydroxypyridin-2-yl]amino}acetate (4): To a 50 mL round bottom flask adapted for magnetic stirring and fitted with a nitrogen inlet tube was charged 5-(3-chlorophenyl)-3-hydroxypyridine-2-carboxylic acid, 3, (1 gm, 4 mmol), N,N'-carbonyldiimidazole (CDI) (0.97 g, 6 mmol) and dimethyl sulfoxide (5 mL). The reaction mixture was stirred at 45° C. for about 1 hour then cooled to room temperature. Glycine methyl ester hydrochloride (1.15 g, 12 mmol) is added followed by the dropwise addition of diisopropylethylamine (3.2 mL, 19 mmol). The mixture was then stirred for 2.5 hours at room temperature after which water (70 mL) was added. The contents of the reaction flask was cooled to 0° C. to 5° C. and 1N HCl was added until the solution pH is approximately 2. The solution was extracted with dichloromethane (100 mL) and the organic layer was dried over $MgSO_4$ for 16 hours. Silica gel (3 g) is added and the solution slurried for 2 hours after which the solids are removed by filtration. The filtrate is concentrated to dryness under reduced pressure and the resulting residue was slurried in methanol (10 mL) for two hours. The resulting solid was collected by filtration and washed with cold methanol (20 mL) then hexane and the resulting cake is dried to afford 0.85 g of the desired product as an off-white solid. The filtrate was treated to afford 0.026 g of the desired product as a second crop. The combined crops afford 0.88 g (68% yield) of the desired product. H NMR (DMSO-$d_6$) δ 12.3 (s, 1H), 9.52 (t, 1H), 8.56 (d, 1H), 7.93 (s, 1H), 7.80 (q, 2H), 7.55 (t, 2H), 4.12 (d, 2H), and 3.69 (s, 3H).

The formulator can readily scale up the above disclosed synthesis. Disclosed herein below is a synthesis wherein the disclosed process is scaled up for commercial use.

Example 2

Methyl {[5-(3-chlorophenyl)-3-hydroxypyridin-2-yl]amino}acetate (4)

Preparation of 5-(3-chlorophenyl)-3-chloro-2-cyanopyridine (1): A 20 L reactor equipped with a mechanical stirrer, dip tube, thermometer and nitrogen inlet was charged with (3-chlorophenyl)boronic acid (550 g, 3.52 mol), 3,5-dichloro-2-cyanopyridine (639 g, 3.69 mol), $K_2CO_3$ (5.5 g, 40 mmol), [1,1'-bis(diphenyphosphino)ferrocene]dichloro-palladium(II) [PdCl$_2$(dppf)] (11.5 g, 140 mmol), and dimethylformamide (3894 g, 4.125 L). The reaction solution was agitated and purged with nitrogen through the dip-tube for 30 minutes. Degassed water (413 g) was then charged to the reaction mixture while maintaining a temperature of less than 50° C. 25 hours. The reaction was determined to be complete due to the disappearance of 3,5-dichloro-2-cyanopyridine as measured by TLC analysis using ethyl acetate/methanol (4:1) as the mobile phase and UV 435 nm to visualize the reaction components. The reaction solution was then cooled to 5° C. and charged with heptane (940 g, 1.375 L) and agitated for 30 minutes. Water (5.5 L) was charged and the mixture was further agitated for 1 hour as the temperature was allowed to rise to 15° C. The solid product was isolated by filtration and washed with water (5.5 L) followed by heptane (18881 g, 2750 ML). The resulting cake was air dried under vacuum for 18 hours and then triturated with a mixture of 2-propanol (6908 g, 8800 mL0 and heptane (1 g, 2200 mL0 at 50° C. for 4 hours, cooled to ambient temperature and then agitated at ambient temperature for 1 hour. The product was then isolated by filtration and washed with cold 2-propanol (3450 g, 4395 mL) followed by heptane (3010 g, 4400 mL). The resulting solid was dried under high vacuum at 40° C. for 64 hours to afford 565.9 g (65% yield) of the desired product as a beige solid. Purity by HPLC was 98.3. $^1$H NMR (DMSO-d$_6$) δ 9.12 (d, 1H), 8.70 (d, 1H), 8.03 (t, 1H) 7.88 (m, 1H), and 7.58 (m, 2H).

Preparation of 5-(3-chlorophenyl)-3-methoxy-2-cyanopyridine (2): A 20 L reactor equipped with a mechanical stirred, condenser, thermometer and nitrogen inlet was charged with 5-(3-chlorophenyl)-3-chloro-2-cyanopyridine, 1, (558 g, 2.24 mol) and sodium methoxide (25% solution in methanol, 726.0 g, 3.36 mol). With agitation, the reaction solution was heated to reflux for 24 hours, resulting in a beige-colored suspension. The reaction was determined to be complete due to the disappearance of 5-(3-chlorophenyl)-3-chloro-2-cyanopyridine as measured by TLC analysis using hexane/ethyl acetate (6:3) as the mobile phase and UV 435 nm to visualize the reaction components. The reaction mixture was cooled to 5° C. and then charged with water (5580 mL). The resulting slurry was agitated for 3 hours at 5° C. The solid product was isolated by filtration and washed with water (5580 mL) until the filtrate had a pH of 7. The filter cake was air dried under vacuum for 16 hours. The filter cake was then charged back to the reactor and triturated in MeOH (2210 g, 2794 mL) for 1 hour at ambient temperature. The solid was collected by filtration and washed with MeOH (882 g, 1116 mL, 5° C.) followed by heptane (205 mL, 300 mL), and dried under high vacuum at 45° C. for 72 hours to afford 448 g (82% yield) of the desired product as an off-white solid. Purity by HPLC was 97.9%. $^1$H NMR (DMSO-d$_6$) δ 8.68 (d, 1H), 8.05 (d, 1H), 8.01 (s, 1H) 7.86 (m, 1H), 7.59 (s, 1H), 7.57 (s, 1H) and 4.09 (s, 3H).

Preparation of 5-(3-chlorophenyl)-3-hydroxypyridine-2-carboxylic acid (3): A 20 L reactor equipped with a mechanical stirrer, condenser, thermometer, nitrogen inlet and 25% aqueous NaOH trap was charged 5-(3-chlorophenyl)-3-methoxy-2-cyanopyridine, 2, (440.6 g, 1.8 mol) and 37% aqueous solution of HCl (5302 g). While being agitated, the reaction solution was heated to 102° C. for 24 hours. Additional 37% aqueous HCl (2653 g) was added followed by agitation for 18 hours at 104° C. The reaction contents was then cooled to 5° C., charged with water (4410 g) and then agitated at 0° C. for 16 hours. The resulting precipitated product was isolated by filtration and washed with water until the filtrate had a pH of 6 (about 8,000 L of water). The filter cake was pulled dry under reduced pressure for 2 hours. The cake was then transferred back into the reactor and triturated in THE (1958 g, 2201 mL) at ambient temperature for 2 hours. The solid product was then isolated by filtration and washed with THE (778 g, 875 mL) and dried under reduced pressure at 5° C. for 48 hours to afford 385 g (89% yield) of the desired product as an off-white solid. HPLC purity was 96.2%. $^1$H NMR (DMSO-d$_6$) δ 8.52 (d, 1H), 7.99 (d, 1H), 7.95 (s, 1H) 7.81 (t, 1H), 7.57 (s, 1H), and 7.55 (s, 1H).

Preparation of methyl {[5-(3-chlorophenyl)-3-hydroxypyridin-2-yl]amino}acetate (4): A 20 L reactor equipped with a mechanical stirrer, condenser, thermometer and nitrogen inlet was charged with 5-(3-chlorophenyl)-3-hydroxypyridine-2-carboxylic acid, 3, (380 g, 1.52 mol) and diisopropylethylamine (DIPEA)(295 g, 2.28 mol). With agitation, the solution was cooled to 3° C. and charged with trimethylacetyl chloride (275.7 g, 2.29 mol) while maintaining a temperature of less than 11° C., The mixture was then agitated at ambient temperature for 2 hours. The mixture was then cooled to 10° C. and charged with a slurry of glycine methyl ester HCl (573.3 g, 4.57 mol) and TH (1689 g, 1900 mL), then charged with DIPEA (590.2 g, 4.57 mol) and agitated at ambient temperature for 16 hours. The mixture was then charged with EtOH (1500 g, 1900 mL) and concentrated under reduced pressure to a reaction volume of about 5.8 L. The EtOH addition and concentration was repeated twice more. Water (3800 g) was then added and the mixture was agitated for 16 hours at ambient temperature. The resulting solid product was isolated by filtration and washed with a mixture of EtOH (300 g, 380 mL) and water (380 g), followed by water (3800 g), dried under reduced pressure for 18 hours at 50° C. to afforded 443 g (91% yield) of the desired product as an off-white solid. Purity by HPLC was 98.9%. $^1$H NMR (DMSO-d$_6$) δ 12.3 (s, 1H), 9.52 (t, 1H), 8.56 (d, 1H), 7.93 (s, 1H), 7.80 (q, 2H), 7.55 (t, 2H), 4.12 (d, 2H), and 3.69 (s, 3H).

Scheme II herein below outlines and Example 2 describes a non-limiting example of the disclosed process for preparing a prolyl hydroxylase inhibitor from an ester prodrug.

Scheme II

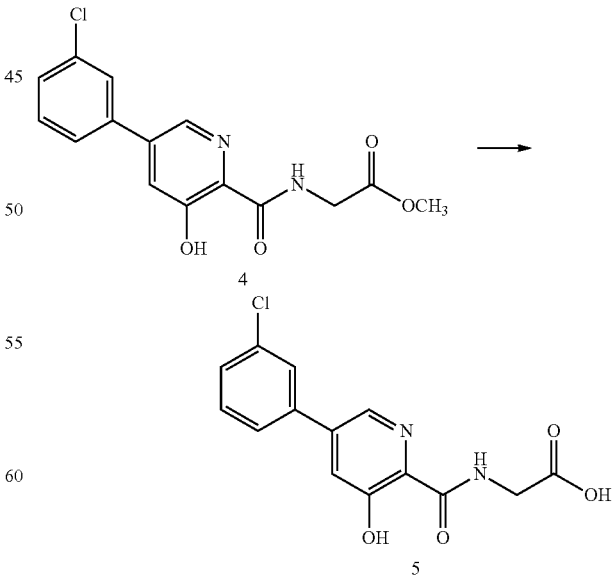

Reagents and conditions: (a) NaOH, THF; 2 hr.

Example 3

{[5-(3-Chlorophenyl)-3-hydroxypyridin-2-yl]amino}acetic acid (5)

Preparation of {[5-(3-chlorophenyl)-3-hydroxypyridin-2-yl]amino}acetic acid (5): To a 50 mL flask is charged methyl {[5-(3-chlorophenyl)-3-hydroxypyridin-2-yl]amino}-acetate, 4, (0.45 g, 1.4 mmol), tetrahydrofuran (4.5 mL) and 1 M NaOH (4.5 mL, 4.5 mmol). The mixture was stirred for 2 hours at room temperature after which it was determined by TLC analysis using hexane/ethyl acetate (6:3) as the mobile phase and UV 435 nm to visualize the reaction components that the reaction was complete. The reaction solution was adjusted to pH 1 with concentrated HCl and the solution was heated at 35° C. under vacuum until all of the tetrahydrofuran had been removed. A slurry forms as the solution is concentrated. With efficient stirring the pH is adjusted to ~2 with the slow addition of 1 M NaOH. The solid which forms was collected by filtration, washed with water, followed by hexane, then dried under vacuum to afford 0.38 g (88% yield) of the desired product as a white solid. $^1$H NMR (DMSO-$d_6$) δ 12.84 (s, 1H), 12.39 (s, 1H), 9.39 (t, 1H), 8.56 (d, 1H), 7.94 (s, 1H), 7.81 (m, 2H), 7.55 (q, 2H), and 4.02 (d, 2H).

The formulator can readily scale up the above disclosed synthesis. Disclosed herein below is a synthesis wherein the disclosed process is scaled up for commercial use.

Example 4

{[5-(3-Chlorophenyl)-3-hydroxypyridin-2-yl]amino}acetic acid (5)

Preparation of {[5-(3-chlorophenyl)-3-hydroxypyridin-2-yl]amino}acetic acid (5): To a 20 L reactor equipped with a mechanical stirrer, condenser, thermometer and nitrogen inlet was charged methyl {[5-(3-chlorophenyl)-3-hydroxypyridin-2-yl]amino}-acetate, 4, (440 g, 1.42 mol), tetrahydrofuran (3912 g, 4400 mL) and 1 M NaOH (4400 mL). The mixture was stirred for 2 hours at room temperature after which it was determined by TLC analysis using hexane/ethyl acetate (6:3) as the mobile phase and UV 435 nm to visualize the reaction components that the reaction was complete. The reaction solution was acidified to a pH of 2 with slow addition of 2M HCl (2359 g). The resulting mixture was concentrated under reduced pressure to a volume of about 7.5 L. Ware (2210 g) was added and the solution cooled to ambient temperature and agitated for 18 hours. The solid product was isolated by filtration and washed with water (6 L). the crude product was transferred back into the reactor and triturated with 2215 g o deionized water at 70° C. for 16 hours. The mixture was cooled to ambient temperature, The solid product was isolated by filtration and washed with water (500 mL) and dried under reduced pressure at 70° C. for 20 hours to afford 368 g (87% yield) of the desired product as an off-white solid. Purity by HPLC was 99.3%. $^1$H NMR (DMSO-$d_6$) δ 12.84 (s, 1H), 12.39 (s, 1H), 9.39 (t, 1H), 8.56 (d, 1H), 7.94 (s, 1H), 7.81 (m, 2H), 7.55 (q, 2H), and 4.02 (d, 2H).

Scheme III herein below outlines and Example 3 describes a non-limiting example of the disclosed process for preparing a prolyl hydroxylase amide prodrug.

Scheme III

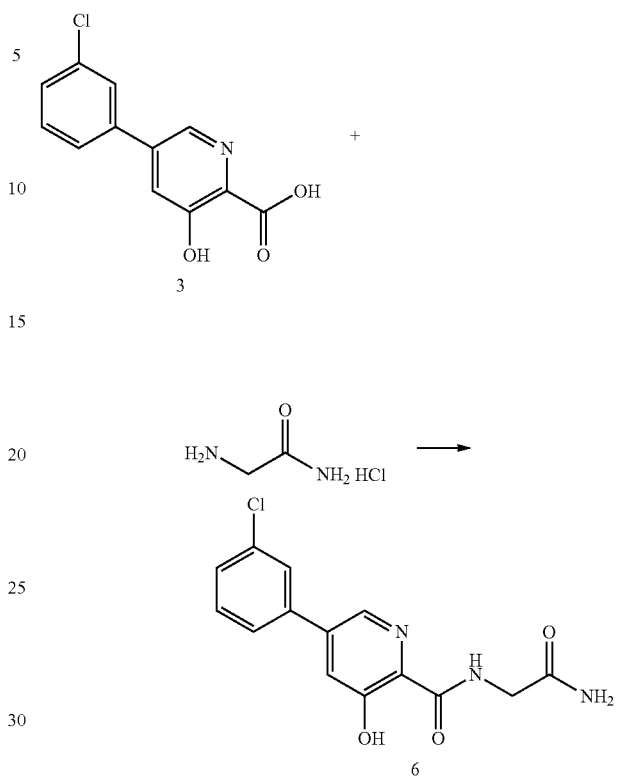

Reagents and conditions: (a) EDCI, HOBt, DIPEA, DMF; rt.

Example 5

5-(3-Chlorophenyl)-N-(2-amino-2-oxoethyl)-3-hydroxylpyridin-2-yl amide

Preparation of 5-(3-chlorophenyl)-N-(2-amino-2-oxoethyl)-3-hydroxylpyridin-2-yl amide (6): To a solution of 5-(3-chlorophenyl)-3-hydroxypyridine-2-carboxylic acid, 3, (749 mg, 3 mmol) in DMF (20 mL) at room temperature under $N_2$ is added 1-(3-dimethyl-aminopropyl)-3-ethylcarbodiimide (EDCI) (0.925 g, 5.97 mmol) and 1-hydroxybenzo-triazole (HOBt) (0.806 g, 5.97 mmol). The resulting solution is stirred for 15 minutes then 2-aminoacetamide hydrochloride (0.66 g, 5.97 mmol) and diisopropylethylamine (1.56 ml, 8.96 mmol) are added. The reaction is monitored by TLC and when the reaction is complete the reaction mixture is concentrated under reduced pressure and $H_2O$ added. The product can be isolated by normal work-up: The following data have been reported for compound (6). $^1$H NMR (250 MHz, DMSO-$d_6$) δ ppm 12.46 (1H, s), 9.17 (1H, t, J=5.9 Hz), 8.55 (1H, d, J=2.0 Hz), 7.93 (1H, d, J=0.9 Hz), 7.75-7.84 (2H, m), 7.49-7.60 (3H, m), 7.18 (1H, s), 3.91 (2H, d, J=5.9 Hz). HPLC-MS: m/z 306 [M+H]$^+$.

Scheme IV herein below depicts a non-limiting example the hydrolysis of an amide pro-drug to a prolyl hydroxylase inhibitor after removal of a $R^{10}$ protecting group.

Scheme IV

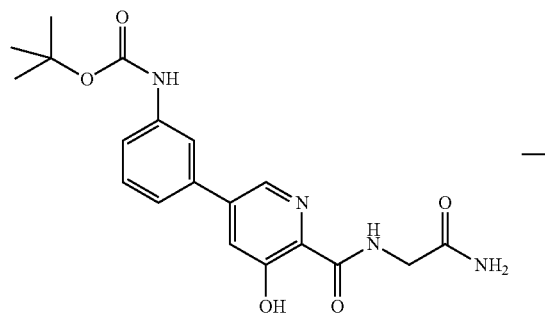

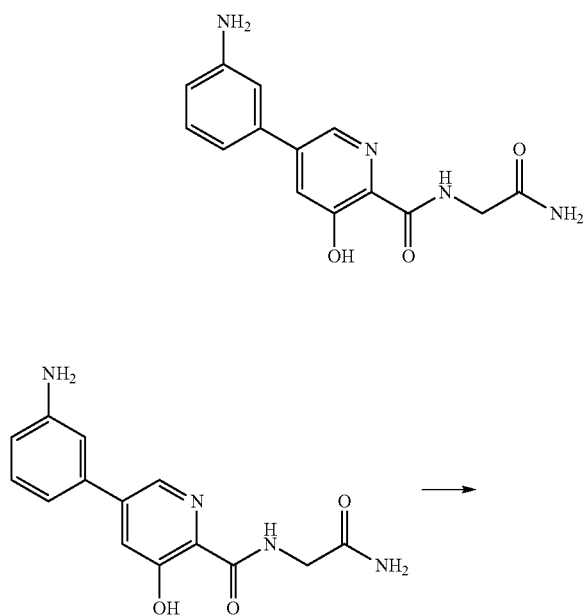

What is claimed is:

1. A process for preparing compound (5):

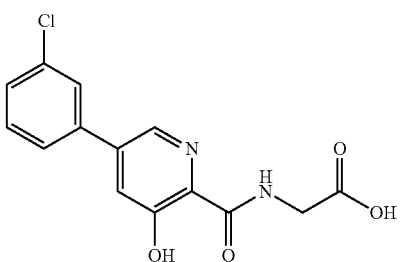

comprising:

A. reacting (3-chlorophenyl)boronic acid:

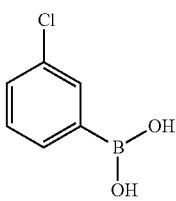

with 3,5-dichloro-2-cyanopyridine:

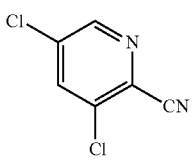

in the presence of a catalyst and a base to form 5-(3-chlorophenyl)-3-chloro-2-cyanopyridine:

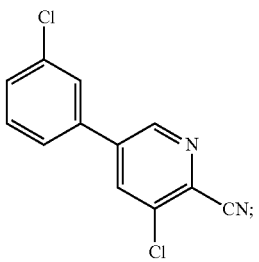 [SMILES: N#Cc1ncc(-c2cccc(Cl)c2)cc1Cl]

B. reacting 5-(3-chlorophenyl)-3-chloro-2-cyanopyridine with sodium methoxide to form 5-(3-chlorophenyl)-3-methoxy-2-cyanopyridine:

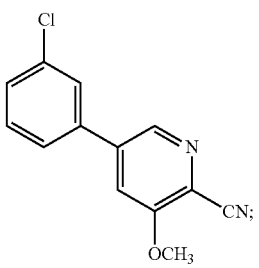 [SMILES: COc1cc(-c2cccc(Cl)c2)cnc1C#N]

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

C. reacting 5-(3-chlorophenyl)-3-methoxy-2-cyanopyridine with hydrobromic acid or hydrochloric acid to form 5-(3-chlorophenyl)-3-hydroxypyridine-2-carboxylic acid:

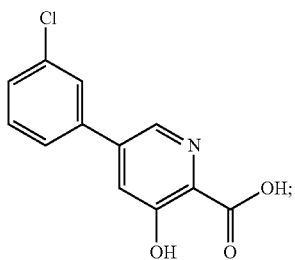 [SMILES: O=C(O)c1ncc(-c2cccc(Cl)c2)cc1O]

D. reacting 5-(3-chlorophenyl)-3-hydroxypyridine-2-carboxylic acid with glycine methyl ester:

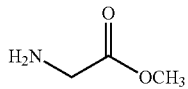

in the presence of a coupling reagent to form methyl {[5-(3-chlorophenyl)-3-hydroxypyridin-2-yl]amino}acetate:

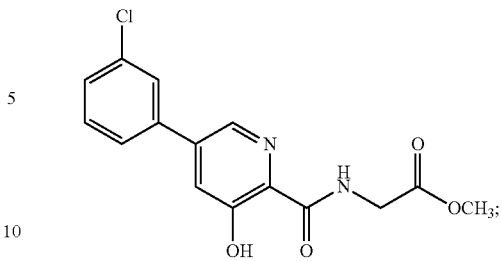

and

E. reacting methyl {[5-(3-chlorophenyl)-3-hydroxypyridin-2-yl]amino}acetate with sodium hydroxide to form compound (5):

(5)

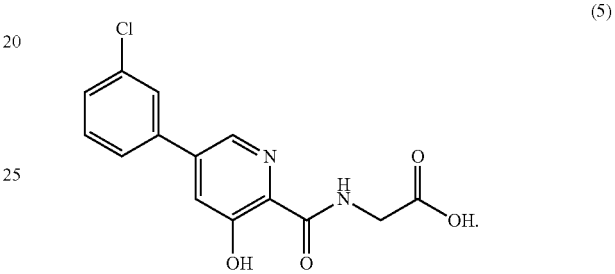

2. The process according to claim 1, wherein the catalyst in step (A) is [1,1'-bis (diphenyphosphino)ferrocene]dichloro palladium(II).

3. The process of claim 1, wherein the base of step (A) is LiOH, NaOH, KOH, Ca(OH)$_2$, Li$_2$CO$_3$, Na$_2$CO$_3$, K$_2$CO$_3$, or CaCO$_3$.

4. The process of claim 3, wherein the base is K$_2$CO$_3$.

5. The process of claim 1, wherein the acid of step (C) is hydrochloric acid.

* * * * *